United States Patent [19]
Jeatran et al.

[11] Patent Number: 5,898,586
[45] Date of Patent: Apr. 27, 1999

[54] METHOD FOR ADMINISTERING CLINICAL TRAIL MATERIAL

[75] Inventors: Thomas L. Jeatran; Roy N. Tamura; James Monroe Solenberg, Jr., all of Indianpolis, Ind.

[73] Assignee: Eli Lilly and Company, Indianapolis, Ind.

[21] Appl. No.: 08/334,411

[22] Filed: Nov. 4, 1994

[51] Int. Cl.$^6$ .................................................. G06F 153/00
[52] U.S. Cl. .................................................................. 705/1
[58] Field of Search ....................... 364/413.02; 235/101, 235/375; 705/1

[56] References Cited

U.S. PATENT DOCUMENTS

| | | | |
|---|---|---|---|
| 4,637,635 | 1/1987 | Levine | 283/101 |
| 4,835,372 | 5/1989 | Gembrich et al. | 235/375 |
| 4,853,521 | 8/1989 | Claeys et al. | 235/375 |
| 5,272,318 | 12/1993 | German | 235/375 |

OTHER PUBLICATIONS

Controlled Clinical Trails, 12:367–377, 1991, ISBN 0197-2456 An Automated Patient Registration and Treatment Randomization System for Multicenter Clinical Trails, Jeffrey P. Krischer et al.
What are Clinical Trials All About?: A Booklet for Patients with Cancer, National Cancer Institute Pamphlet, Jun. 1992.

Primary Examiner—Gail O. Hayes
Assistant Examiner—Diane Mizrahi
Attorney, Agent, or Firm—Woodard, Emhardt, Naughton, Moriarty & McNett

[57] ABSTRACT

A method for administering clinical trial material includes a method for administering clinical trial material, comprising the steps of providing at least one kit containing a plurality of bottles, each with two separate indicia appearing thereon, at least one of the bottles containing a quantity of clinical material at a first dosage, and another at least one of the bottles containing one of a quantity of the clinical material at a second dosage, a quantity of control drug and a placebo; identifying first and second study groups, each providing a treatment schedule for administering dosages of at least one of the clinical material, the control drug and the placebo, the first and second study groups having different treatment schedules; randomly assigning patients to the first and second study groups; assigning at least one investigator to administer the contents of the plurality of bottles; telephone means accessible to the investigator and having a keypad; providing sponsor computer means including telephony capabilities and for storing information, disseminating information, and instructions over the telephone to the investigators, and for receiving information and instructions over the telephone from the investigators, the computer means operable, upon being contacted by the investigator, to identify which of the plurality of bottle of the kit is to be disseminated to an identified patient, but requiring the investigator to confirm selection of the correct bottle by requesting the investigator to enter into the telephone keypad one of the identifying indicia appearing on the selected bottle; and distributing the at least one kit to said investigator.

11 Claims, 33 Drawing Sheets

Introduction

Assign Medication - Find Medication

Collect Study Data - Modify Visit Data

127

This function is unique to each study.

Fig. 8

Discontinue Patient 160

Identify Patient - Sex

Patient Status - Enrollment Birth Data

Process Patient Visit - Randomize
128

• Check for End of Call
  136

• • End Call
   ‿
   81

METHOD FOR ADMINISTERING CLINICAL TRAIL MATERIAL

FIELD OF THE INVENTION

The present invention relates to the field of drug evaluation through clinical trial studies, and more specifically, to a method for assigning treatments, dispensing drugs, monitoring clinical trial materials, and obtaining data from clinical trials.

BACKGROUND OF THE INVENTION

Clinical trials of new drugs provide critical data on the drug's effectiveness, dosage requirements and possible adverse side effects. Unlike marketing strategies developed and applied to the introduction and sales of a new drug, it is desired and sometimes necessary in clinical studies to conceal or "blind" the drug to be studied. Blinding the clinical study is believed necessary to prevent bias from the participants—patients, investigators and sponsors—from comprising the results. Blinded studies can also enhance marketability of a product by more credibly demonstrating the favorable health and economic advantages, such as greater therapeutic efficacy and fewer adverse effects, when compared with a marketed drug or placebo. In addition, many governments require blinded clinical studies for approval of a new drug. (See 21 C.F.R. 314.26 and European Union's Directive 91/507/EEC).

Common types of blinding used in clinical studies are outlined in Table 1:

TABLE 1

Definitions of Common Types of Clinical Studies
OPEN LABEL: No blinding is used; participants know the identity of the treatment.
SINGLE BLIND: Only the patient is blinded.
DOUBLE BLIND: The patient and clinical investigator are blinded.
TRIPLE BLIND: The patient, the clinical investigator and the sponsor are all blinded.

Effective blinding requires each aspect of the treatment—dosage form, packaging, labelling, dosage interval, dosage strength and dosage composition—to appear the same. That is, none of the participants to the study should be able to discern whether they are taking placebo, one or more strengths of investigational drug, or one or more strengths of comparator drug (the comparator or control drug is a marketed drug commonly used for the disease being studied). The blinding procedure is further complicated by the need to comply with all aspects of Good Manufacturing Practices (GMP) requirements.

Traditional methods of conducting blind clinical studies include a group of patients monitored by an investigator or investigators. For example, in a study with a total of 300 patients, each of six investigators might have 50 patients. The investigators would each receive boxes of drug, or "kits". Each kit would be patient specific. The kits will contain all of the required treatment for a specific patient for the duration of the clinical study. Traditional kits have random numbers which will randomize the patients to one of the different treatments in the study. The "kits" are thus utilized to randomly assign patients to one of the treatment regimens in the study. If the study design contemplates dosage changes for patients during the study, the kit would also include sufficient packages of each possible dosage change that might be needed by a patient during the study.

In practice, as little as ⅓ of the medication in a patient kit might be used. After the study is complete, the remaining ⅔ of the medication would be discarded. Also, some of the patients will drop out of the study over time. In total, as much as 75% of the drug in the patient kits may be wasted. Obviously, traditional blinded clinical studies are saddled with a tremendous waste of resources, time and money to prepare and conduct the study. In some cases, scarce supplies of the investigational drug may actually preclude doing a definitive blinded study.

An improvement to the described method is to provide each investigator with an approximation of the amount of packaged drug sufficient to treat all the patients in the study, this approximation NOT being patient specific. Using a statistically derived estimate of the quantities required for the entire study, boxes are filled with randomly numbered packages of each drug and dosage. A computer database is used to assign and keep track of the patient randomization and dosage information. When each patient is to receive his or her dosage, the investigator accesses the database and enters the patient control number. The computer database then tells the investigator which package of drug to dispense. The contents of each package of medication are stored in the database by the random number. The computer can thus tell the investigator which randomly numbered bottle corresponds to the treatment the patient requires. Neither the investigator nor the patient will know which therapy is dispensed to the patient. In this way, complete, patient specific kits, large portions of which would be wasted, are not necessary. Instead, the doses, whether active or placebos are provided en masse and will better approximate the actual usage of medications in the study.

While this improvement does reduce the waste associated with patient specific kits, it nevertheless has drawbacks such as permitting dispensing of the wrong bottle. For example, where the physician investigator is instructed to administer bottle "X", he could mistakenly select and administer bottle "Y" and not realize the error until bottle "Y" is required sometime later, or never. While such studies have improved the efficacy and ease of drug evaluation, they are still largely one dimensional and require traditional analysis methods and possibly follow-up studies. These studies are also still expensive and time-consuming.

What is needed is a method for conducting blinded clinical studies which permits for improved verification of the intended treatment and patient qualification, and which facilitates improved, cheaper and more efficient administration of the drug analysis.

SUMMARY OF THE INVENTION

Generally speaking, there is provided a method for administering clinical trial materials includes a computer system which is programmed and adapted to communicate with investigators field over the telephone. Information may thereby be received and distributed instantaneously and may be stored in a common database so that the progress of the study may be determined at any moment.

The method includes providing at least one kit containing a plurality of bottles, each with two separate indicia appearing thereon, at least one of the bottles containing a quantity of clinical material at a first dosage, and another at least one of the bottles containing one of a quantity of the clinical material at a second dosage, a quantity of control drug and a placebo; identifying first and second study groups, each providing a treatment schedule for administering dosages of at least one of the clinical material, the control drug and the placebo, the first and second study groups having different treatment schedules; randomly assigning patients to the first and second study groups; assigning at least one investigator to administer the contents of the plurality of bottles; telephone means accessible to the investigator and having a keypad; providing sponsor computer means including telephony capabilities and for storing information, disseminating information, and instructions over the telephone to the investigators, and for receiving information and instructions over the telephone from the investigators, the computer means operable, upon being contacted by the investigator, to identify which of the plurality of bottle of the kit is to be disseminated to an identified patient, but requiring the investigator to confim selection of the correct bottle by requesting the investigator to enter into the telephone keypad one of the identifying indicia appearing on the selected bottle; and distributing the at least one kit to said investigator.

It is an object of the present invention to provide an improved procedure for administering clinical trial materials.

It is also an object of the present invention to provide a method for administering clinical trial materials in a cheaper and more efficient manner.

It is another object of the present invention to provide a method for administering clinical trial materials which more quickly determines the beneficial or deleterious effects of a new drug.

Further objects and advantages of the present invention will become apparent from the following description of the preferred embodiment.

BRIEF DESCRIPTION OF THE DRAWINGS

FIGS. 4–33 comprise a flowchart of a computer program for the sponsor which controls the treatment assignment, information collection and storage and dissemination of information and instructions which governs the entire study.

DESCRIPTION OF THE PREFERRED EMBODIMENT

Figure 1:
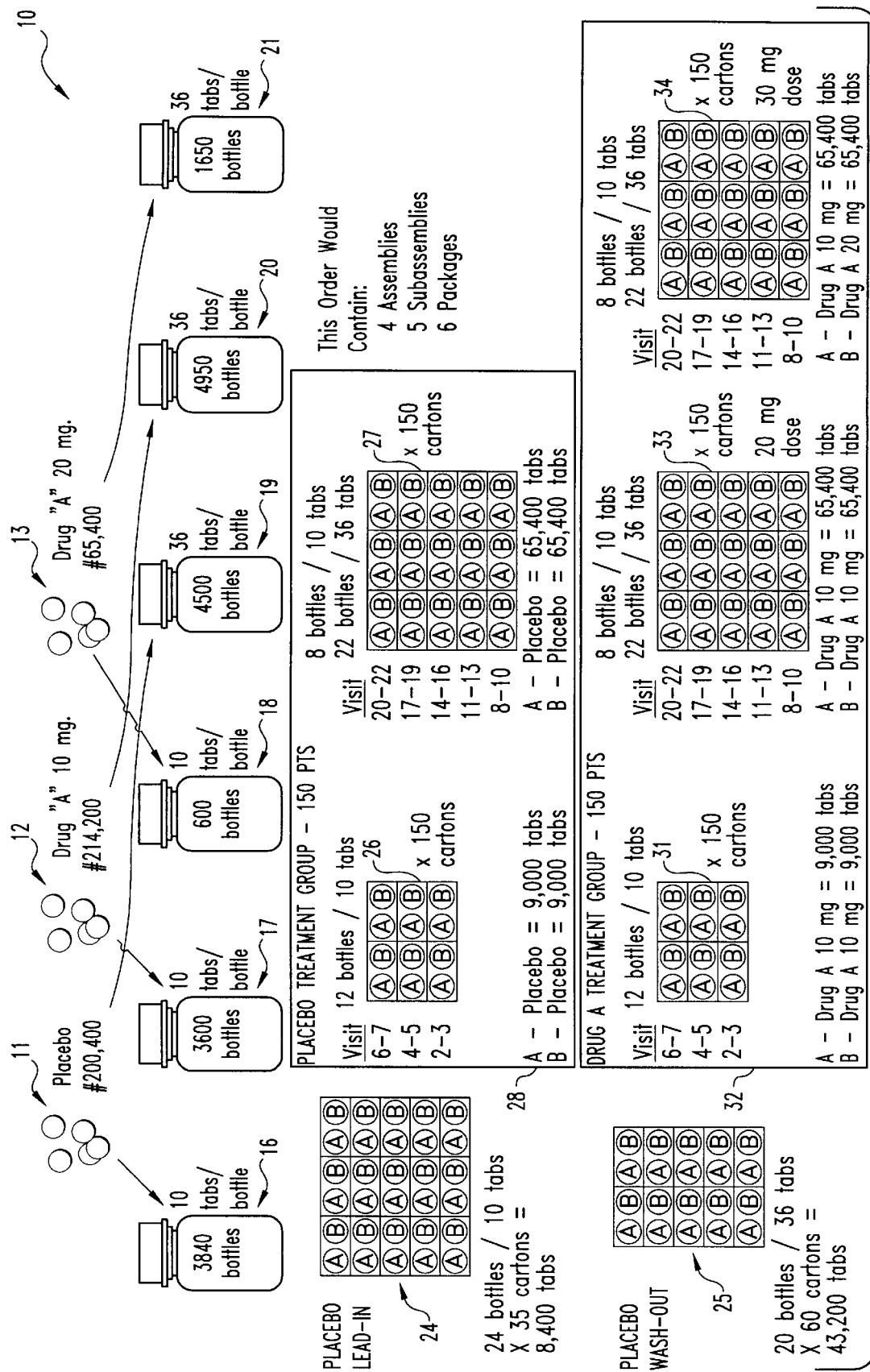
FIG. 1 is a diagram of the assembly of materials necessary for a 300 patient clinical study of a new drug "A" in accordance with the prior art method of conducting clinical studies of new medication.

For the purposes of promoting an understanding of the principles of the invention, reference will now be made to the embodiment illustrated in the drawings and specific language will be used to describe the same. It will nevertheless be understood that no limitation of the scope of the invention is thereby intended, and that alterations and further modifications in the illustrated device, and such further applications of the principles of the invention as illustrated therein are contemplated as would normally occur to one skilled in the art to which the invention relates.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

The standard method of packaging clinical trial material for double-blind studies is to prepare a complete kit for each potential patient. Patient or kit numbers for each treatment group are assigned from random tables. There are several disadvantages associated with this otherwise effective method. First, material (drugs and/or placebos) are prepared and distributed for each patient for the duration of the entire course of therapy (i.e., for six months or one year). If the patient drops out after only one week, for example, the remainder of his material is wasted. (Strict FDA guidelines governing drug preparation, packaging and handling prevent the remainder of the prematurely departing patient's material from being used). Second in many clinical studies, dosages are "titrated." That is, after the initial dosage is established, the concentrations of subsequent dosages may be increased or decreased according to individual requirements of the patients and/or the evaluation of the physician who balances efficacy and adverse effects. This requires additional and varied dosages, most of which are not taken by the patient and are discarded.

Further, such studies are usually conducted in a double- or triple-blind manner. (Common types of blinding used in clinical studies are Open Label—no blinding is used and all participants know the identity of the treatment; Single Blind—only the patient is blinded; Double Blind—the patient and clinical investigator are blinded; and, Triple Blind—the patient, the clinical investigator and the sponsor are all blinded.) Blinding requires 3 to 4 times as much New Drug Substance, which is often in short supply, expensive or both.

Referring to FIG. 1, there is shown a diagram 10 of the assembly of materials necessary for a typical clinical study of a new drug "A" in accordance with the prior art method of conducting clinical studies of new medication. A total of 200,400 placebos 11 are required along with 214,200 tablets of drug A 12 at 10 mg and 65,400 tablets of drug A 13 at 20 mg, all of which are distributed into a total of 19,140 bottles 16–21 in the dosages and numbers shown. Eight hundred and forty 10-tablet placebo bottles 16 and 1200 36-tablet placebo bottles 19 are arranged in 35 cartons 24 and 60 cartons 25, respectively, as shown, for placebo lead-in and wash-out portions of the study. Eighteen hundred 10-tablet placebo bottles 16 are arranged in 150 cartons 26 for the initial study phase of the placebo treatment group 28, and the remaining 1200 10-tablet placebos and 3300 36-tablet placebo bottles are arranged in 150 carbons 27, as shown, for the maintenance phase of placebo treatment group 28. Eighteen hundred 10-tablet bottles 17 of 10 mg drug A are arranged in 150 cartons 31 for the initial phase of the Drug A treatment group 32. Twelve hundred 10-tablet bottles 17 of 10 mg drug A and 3300 36-tablet bottles 20 of the 10 mg drug A are arranged as shown in each of 150 carbons 33 for the maintenance phase of the Drug A treatment group 32. A second set of 150 cartons 34 is also provided, each carton 34 containing bottles of drug A as: 4 10-tablet bottles 17 at 10 mg; 4 10-tablet bottles 18 at 20 mg; 11 36-tablet bottles at 10 mg; and, 11 36-tablet bottles at 20 mg. These last 150 cartons 34 account for the remaining 600 bottles 17, 600 bottles 18, 1650 bottles 20 and 1650 bottles 21. Once the 300 patients for this study are selected and assigned at random to the two groups 28 and 32, each is assigned a complete set of cartons. That is, each patient in Placebo Treatment Group 28 is assigned one carton 26 and one carton 27, and each patient in Drug A Treatment Group 32 is assigned one each of cartons 31, 33 and 34. The physician investigator must store, account for and manipulate all 845 cartons 24, 25, 26, 27, 31, 33, and 34.

Figure 2:
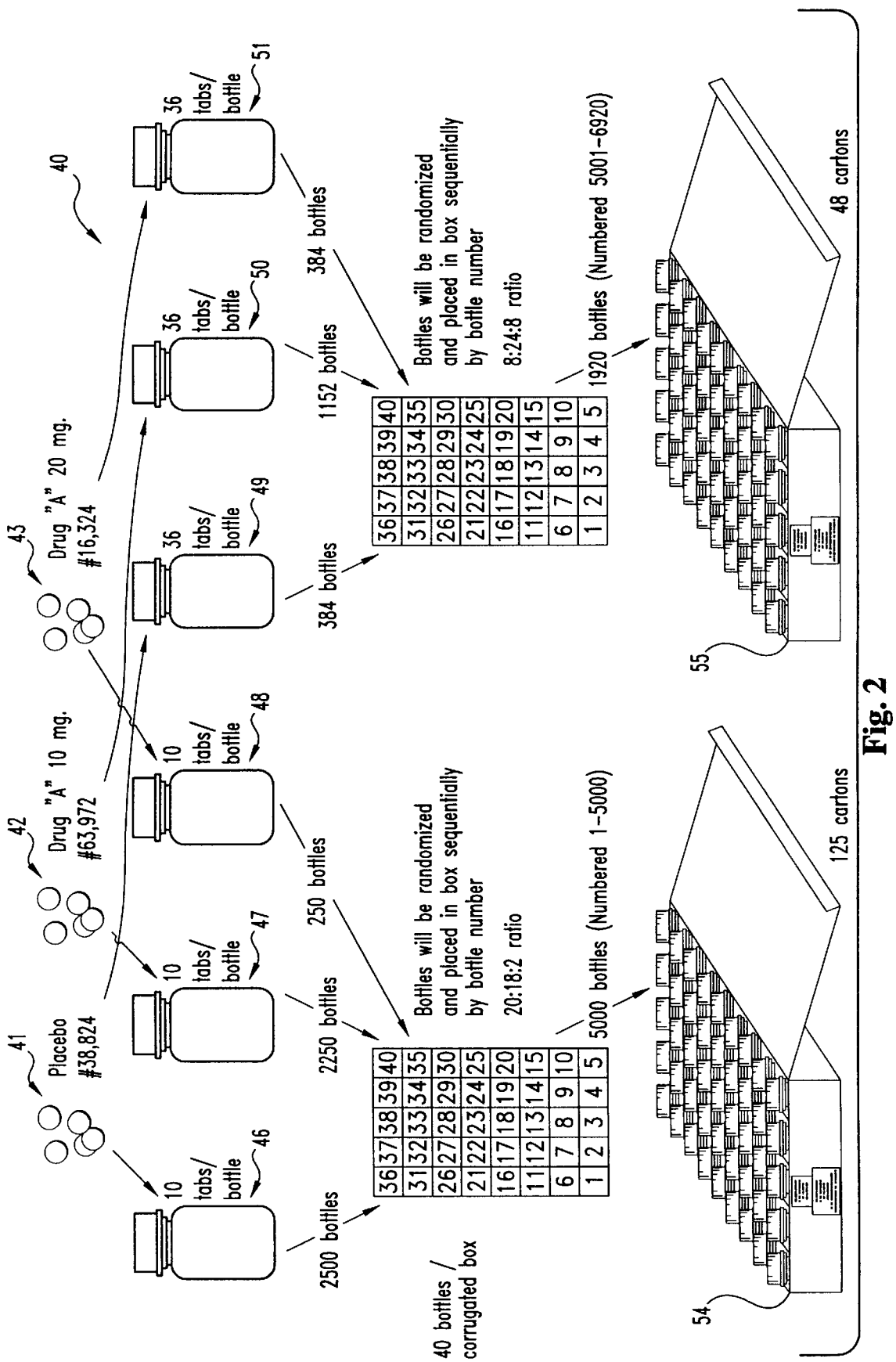
FIG. 2 is a diagram of the assembly of materials necessary for a 300 patient clinical study of a the new drug "A" of FIG. 1 in accordance with the preferred embodiment of the present invention.

Referring now to FIG. 2, there is shown a diagram 40 of the assembly of materials necessary for a clinical study of the same drug A of FIG. 1, also capable of including 300 patient participants. (Packaging forms other than bottles are contemplated herein, such as but not limited to, boxes, pouches and blister cards. Likewise, clinical material may include a variety of forms, such as but not limited to, pills, capsules, tablets, powder and liquid.) A total of 38,824 placebos 41 are required along with 63,972 tablets 42 of drug A at 10 mg and 16,324 tablets 43 of drug A at 20 mg, all of which are distributed in a total of 6,920 bottles 46–51 in the dosages and numbers shown. One hundred and twenty five cartons 54 are then prepared, each containing 40 sequentially numbered bottles, as shown. The 40 bottles comprise, in a randomized assignment, 20 10-tablet placebo bottles 46, 18 10-tablet bottles of 10 mg drug A, and 2 10-tablet bottles of 20 mg drug A. Cartons 54 are for the initial phase of the study. Forty-eight cartons 55 are prepared for the maintenance phase of the study, each carton 55 also containing 40 sequentially numbered bottles, as shown. The 40 bottles comprise, in a randomized assignment, 8 36-tablet placebo bottles 49, 24 36-tablet bottles 50 of 10 mg drug A, and 8 36-tablet bottles 51 of 20 mg drug A. Each investigator administering the study of the present invention must only store, account for and manipulate 173 cartons and 6,920 bottles, as opposed to the 845 cartons and 19,140 bottles of the study method of FIG. 1. All randomizations, dose titrations, and patient assignments and withdrawals may be accommodated in the greatly reduced set of materials shown in FIG. 2. Of course, the need may still arise from time to time where the investigator will need additional materials. These may be ordered on an as needed basis, but, due to the computer interaction described herein, the sponsor should be alerted to an impending shortage, and additional materials should arrive well before the shortage is encountered. Manipulation of the study materials of the 173 cartons 54 and 55 will now be described.

Figure 3:
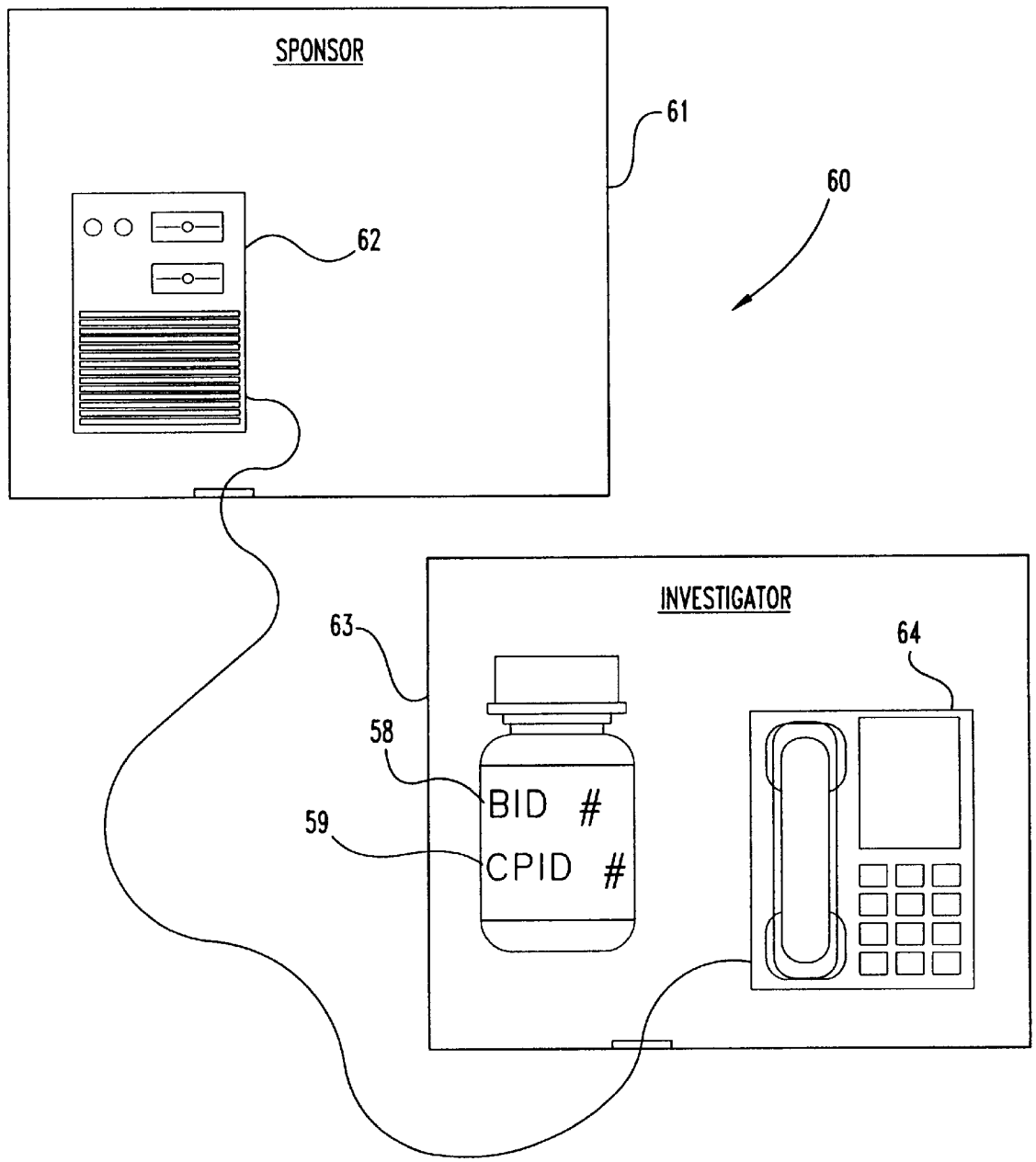
FIG. 3 is a diagram of the interaction between the sponsor of the subject new drug "A" and a remote investigator of the clinical study of FIG. 2.
Figure 4:
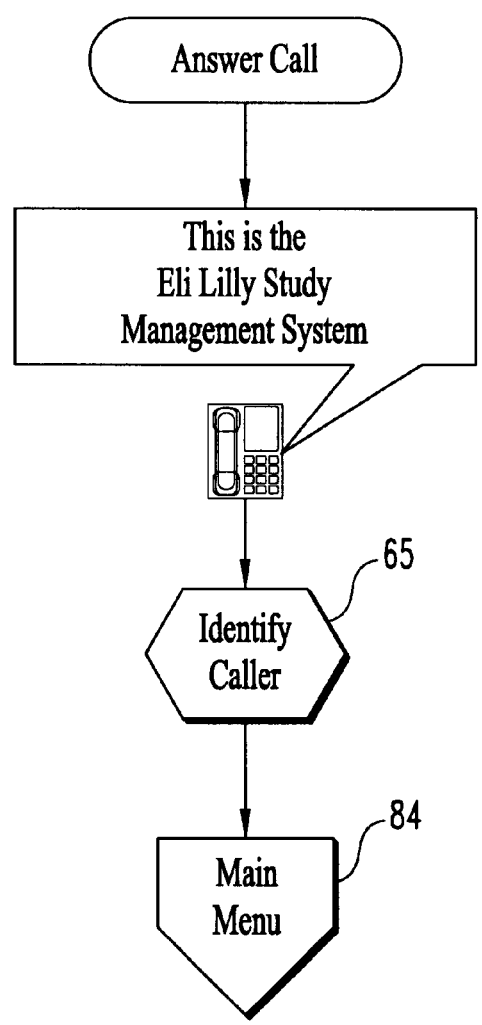

Referring to FIG. 3, communication with the investigator within the study is achieved through a Voice Response Clinical Trial Dispensing System 60. The sponsor 61 of the clinical trial maintains a computer 62 which has loaded thereon a program controlling the collection, storage and dissemination of information and instructions which governs the entire study. Shown in FIGS. 4–33 is a flow chart outlining the program contained on computer 62 in one preferred embodiment of the present invention. The particular program embodied in FIGS. 4–33 is designed to govern the clinical study of a new drug and includes provisions for titrating the dosage of the patient during the study according to the patient's progress in response to his or her dosage. Both the medical status of the patient prior to the study and the progress of the patient during the study are measured through evaluation or testing, the results of which are reflected by a rating or score. In the present embodiment, each patient's score, entered by the investigator, affects both the patient's entry randomization to the study and the possible dose titration as he progresses through the study. The present invention also provides in the program of FIGS. 4–33 for interaction between the investigator and the computer to first identify, and then verify the correct bottle to be administered to the patient, and to identify bad, missing or otherwise corrupt bottles in the investigator's cartons. In this way, the sponsor can, at any time, monitor and evaluate the progress of the study and the specific needs of all of the investigators for additional materials.

The present invention further provides for adaptive randomization, or biasing the randomization of new entrants to the study in response to the new drug's apparent efficacy in the patients as they complete the study. That is, a standard entry randomization of 300 patients will contain just as many chances (150) to enter the new drug treatment group as there are to be assigned to the placebo group (150). In an adaptive randomization, as patients on the new drug finish the study with positive recoveries, the chance for future patients to be randomized to the new drug group (as opposed to the placebo group) will be increased. In this way, a new drug which exhibits positive results consistently will create an entry randomization which quickly results in more people receiving the new drug. Upon their positive responses, the entry randomization for subsequent entry patients will produce an even larger number of patients assigned to the new drug group. On the other hand, a drug which shows early signs of failure or adverse side effects will be noted by the investigator and will help bias the entry randomization for new patients away from the new drug. This not only accelerates the study process, but it also meets public policy by more quickly providing access to effective drugs to those in need and to more quickly withdrawing access to ineffective or adversely effective drugs.

The present invention further includes means for ensuring the investigator has selected the correct bottle as instructed by the sponsor computer. Each bottle is provided with two identifying numbers, a BID and a CPID, 58 and 59, respectively. As will be described herein and as embodied in the flowchart of FIGS. 4–33, the investigator is directed to select a bottle by its BID number 58. The investigator is then requested to enter the CPID number 59 appearing on the bottle he has withdrawn. The sponsor computer compares the BID and CPID numbers 58 and 59. If they do not match, there is either an error with the materials or the investigator has selected the incorrect bottle. In either event, corruption of the study is avoided as the sponsor computer can direct the investigator to select another bottle, as opposed to learning later that an incorrect tablet or dosage was administered to one of the patients.

In addition to the foregoing, the present invention also provides for enrollment criteria verification, collection of patient response information, and changing of the individual patient treatment during the study based on the specific criteria. Each study includes a set of specific minimum standards or enrollment criteria that each participant or patient must meet to be included in the study. These criteria may include a number of factors relating to the particular condition to which the study drug is intended to effect, the current and past health history of the patient, and the patient's score (as described above). The present invention provides for direct input of information by the remote investigator through his or any telephone, incorporation and analysis of such input by the sponsor computer and immediate notification or rejection of verification to the investigator.

During the study, progress of each patient within his or her assigned treatment group is monitored by the investigator and reported with the present invention for collection and analysis by the sponsor. This enables the sponsor to selectively change the individual patient treatment during the study based upon criteria established in the study design. For example, a particular patient P1 coming into the study may need a "score" of 17 to be admitted. P1 comes in with a score of 24 and is therefore admitted. After 7 visits, with dosages of 10 mg, P1's score has not been reduced by at least ⅓. According to the criteria established at the creation of the study, he will automatically be re-randomized to either continue at 10 mg or to escalate to 20 mg. This permits the sponsor the opportunity to see if a higher dosage will be more effective for patients that do not respond to lower dosages. Importantly, neither the investigator nor the patient will ever know that the dosage was in any way modified, thus maintaining the integrity of the study while greatly expanding the extent of knowledge gained about the effects of the study drug. The present invention permits a variety of options in administering the study in view of the collected patient response information. In the above scenario for example, after collecting the patient response after a certain number of visits, the patient's dosage could be titrated, that is, adjusted specifically up or down in response to the patient's progress, or the patient could be re-randomized to an entirely different treatment group. The flexibility afforded by the present invention permits creation of an infinite number of study parameter permutations, which in turn leads to faster verification of drug efficacy, decreased cost in analyzing new drugs, and an increasing probability that patients in the study groups will receive effective medication as early as possible.

An endless variety of different languages can be used to create a program from the flowchart of FIGS. 4–33, and no one language is believed, in general, to be preferred over the other. The program was originally written primarily in Scriptbuilder with some portions written in SQL*Plus while some portions, such as the randomization routines, were written in C. This was to capitalize on the benefits afforded by those particular programs. The original program was written for a computer identified as an AT&T Conversant MAP40. In one preferred embodiment, computer 62 comprises a Sun 1000E computer preferably with 10 gigabytes of memory and 384 megabytes of random access memory and an uninterruptable power supply. The telephone server comprises a Voicetek VTK®/Rackmount voice response unit for processing the incoming and outgoing telephone information. The telephony capabilities, provided in computer 62, enable computer 62 to communicate by the Voicetek unit with the investigators over the phone by the pressing of designated buttons or keys of the phone keypad as directed by the computer. The computer is equiped to play pre-recorded, digitally created or similarly configured statements, over the phone, to relay information and instructions to the investigators. Other hardware and software packages are believed to be usable to practice the present invention.

While a telephone is used herein to provide communication between the investigator and the sponsor computer, the present invention also contemplates using other means such as, but not limited to, wireless communications and computer networking.

While the flowchart of FIGS. 4–33 is believed to be self-explanatory as to the operation and interaction among the sponsor computer, the investigator, his patients, and their response to treatment, a general explanation of the operation of the present invention will now be had with reference to FIGS. 1–3 and the flowchart of FIGS. 4–33.

Figure 13:
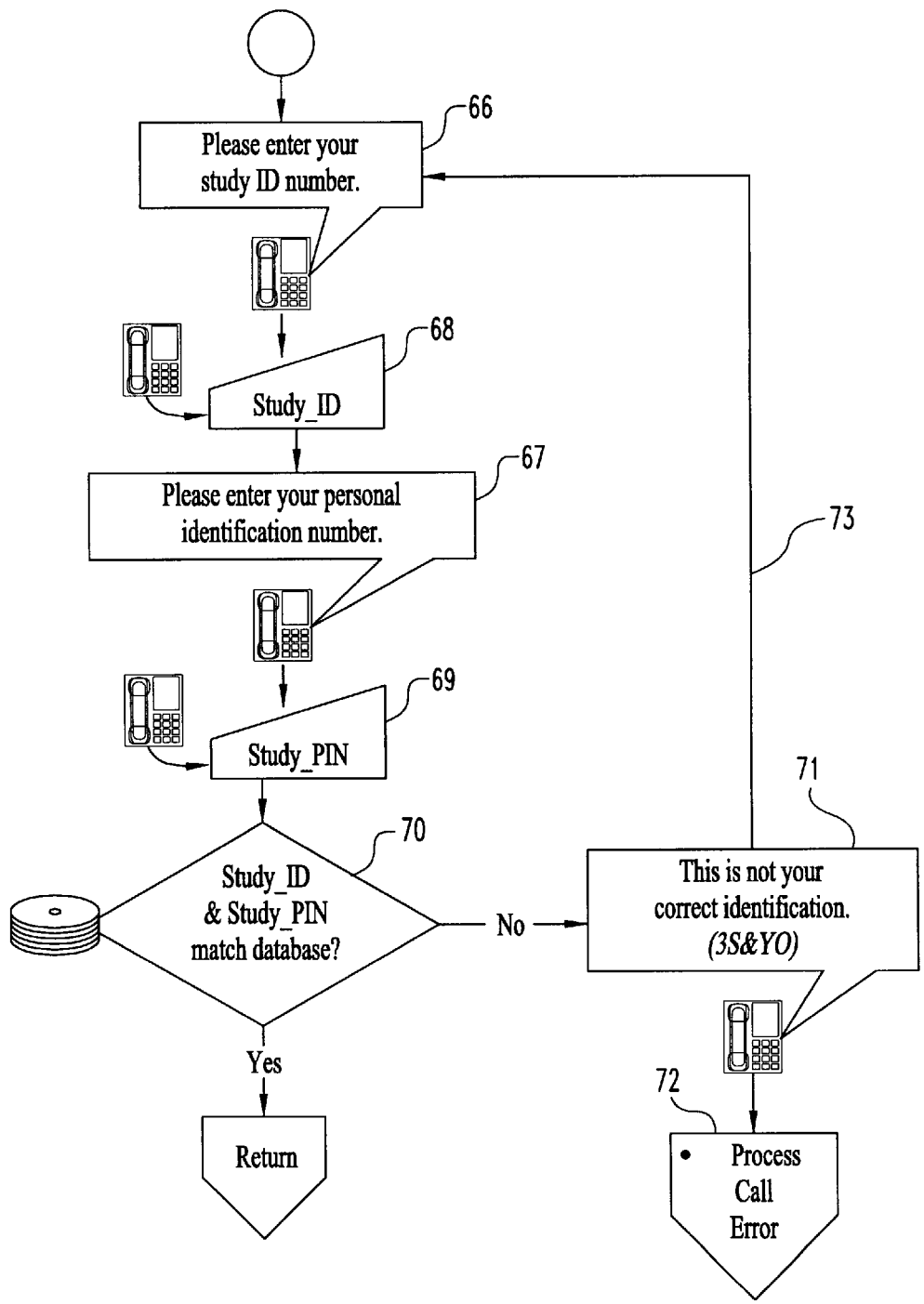
Figure 14:
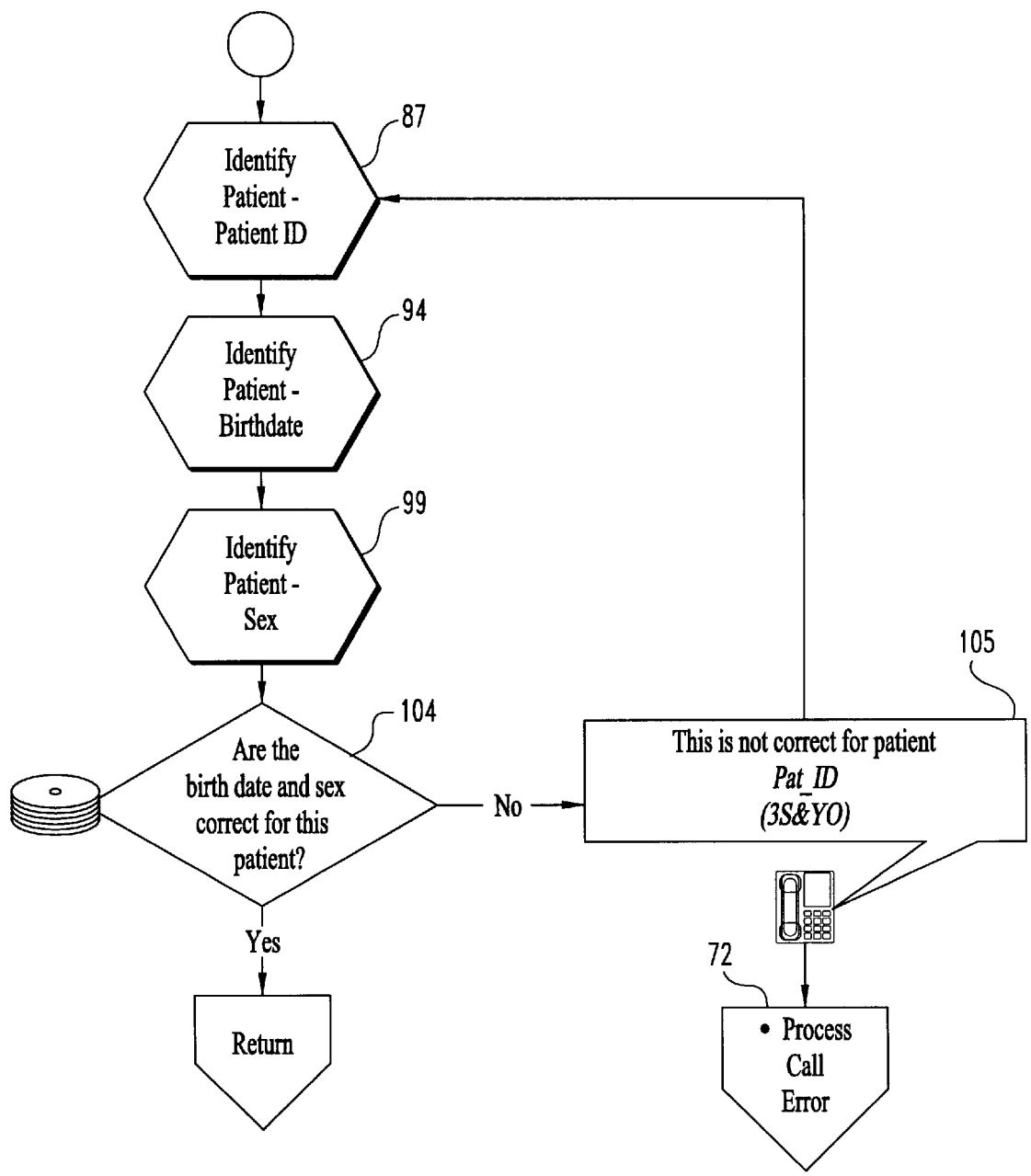
Figure 31:
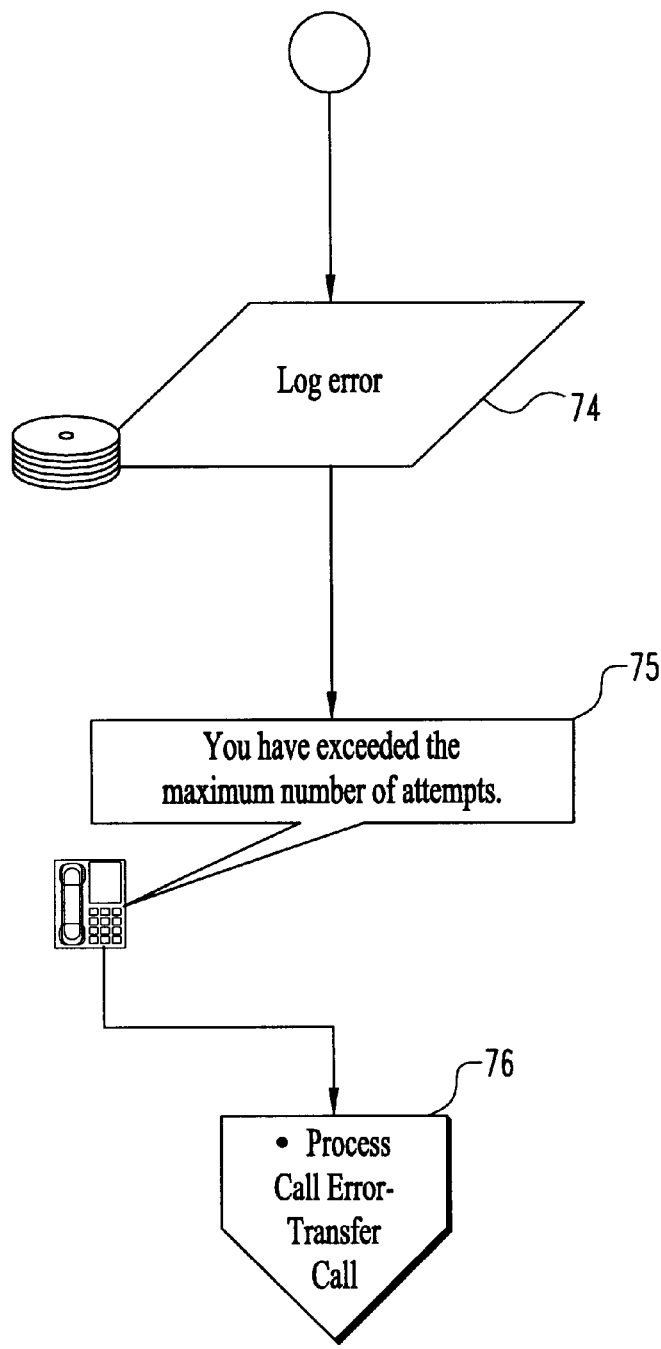
Figure 32:
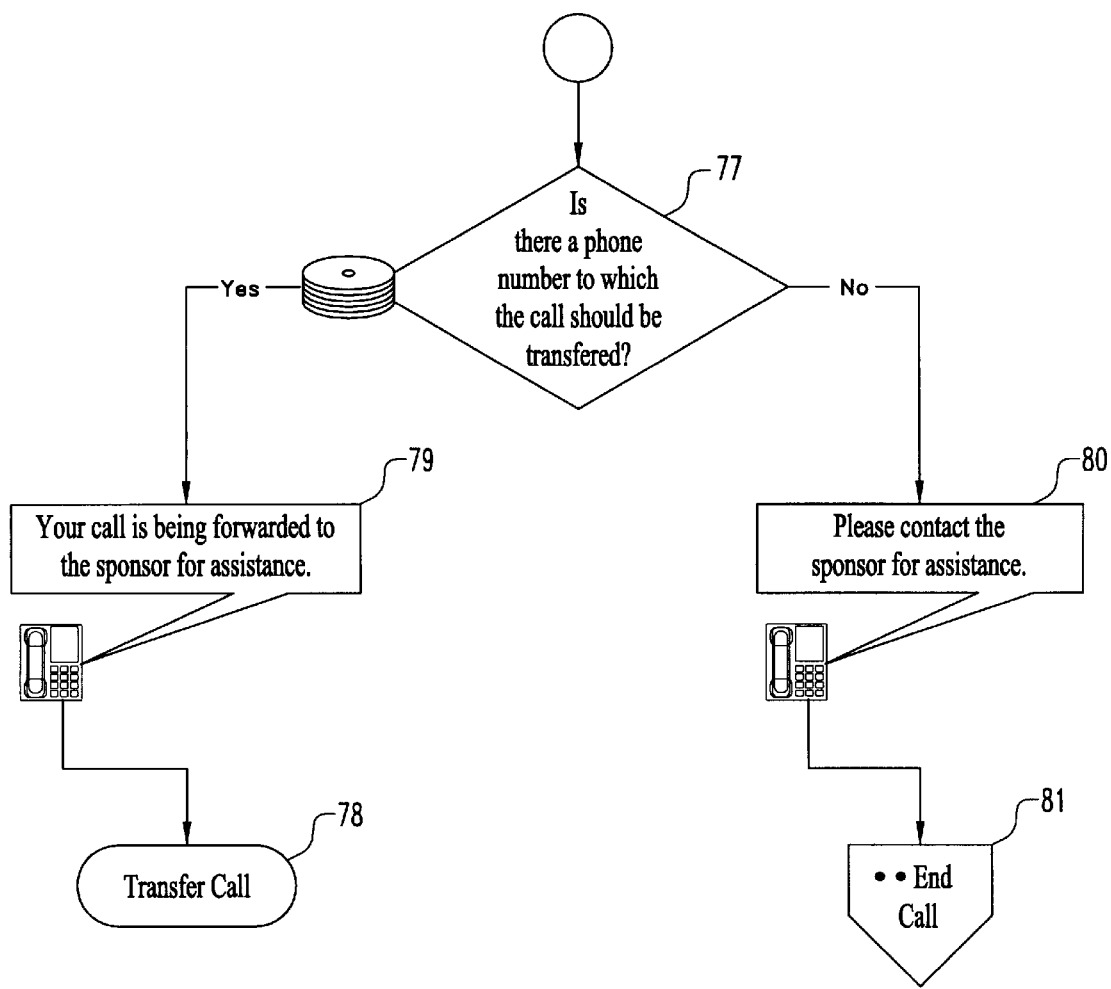
Figure 33:
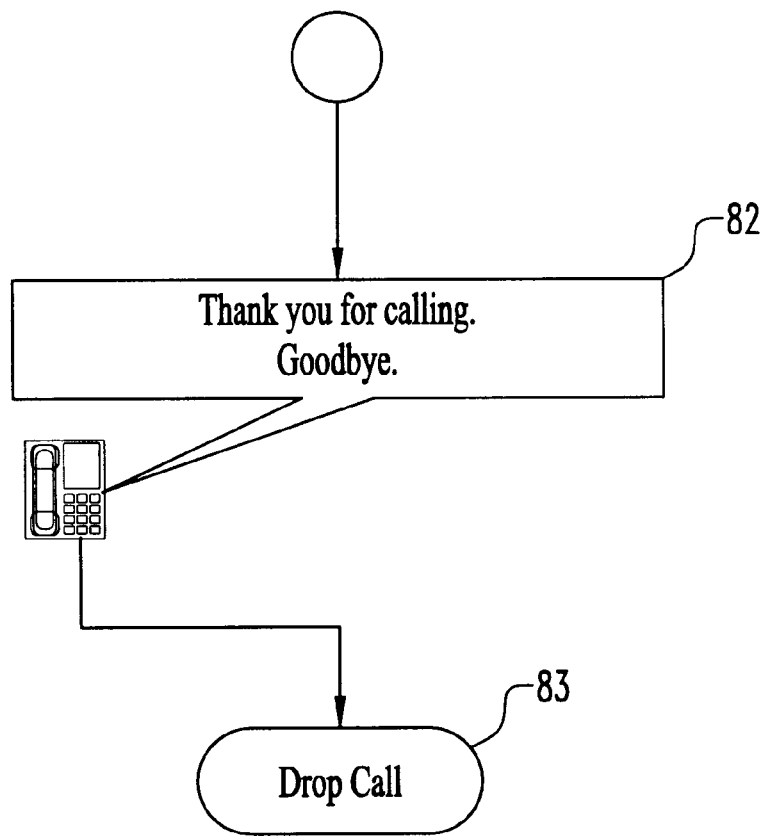

As shown in FIG. 3, an investigator, at her own office 63 or site of study management, initiates contact by calling on a standard Touch Tone telephone 64 to connect over standard telephone cabling (or satellite, as extant) with the sponsor's host computer 62. The computer then greets the caller (FIG. 4) and proceeds to a caller identification subroutine 65. Referring to FIG. 13, the caller is asked to enter her study ID 66 and personal identification number 67. After she enters these numbers (at 68 and 69), if they do not match up with those in the computer's database 70, the computer notifies the caller of the error 71 and, if this error has not exceeded a predetermined number of times, the caller is allowed to try again 73. If the caller has failed to enter either the valid study ID number or personal identification number more than the allotted number of times, the sponsor computer proceeds to the Process Call Error subroutine 72. Referring to FIG. 31, the computer logs the failed attempts 74, notifies the caller 75 and proceeds to the Process Call Error—Transfer Call subroutine 76. Referring to FIG. 32, if the study provides for on-line assistance at this point 77 to the caller, the call is transferred to that assistance 78 and the caller is notified of this 79. If no assistance is available, the caller is directed instead to contact her sponsor directly 80 and the End Call subroutine 81 is run. Referring to FIG. 33 the caller is thanked 82 and the call is dropped 83.

Figure 18:
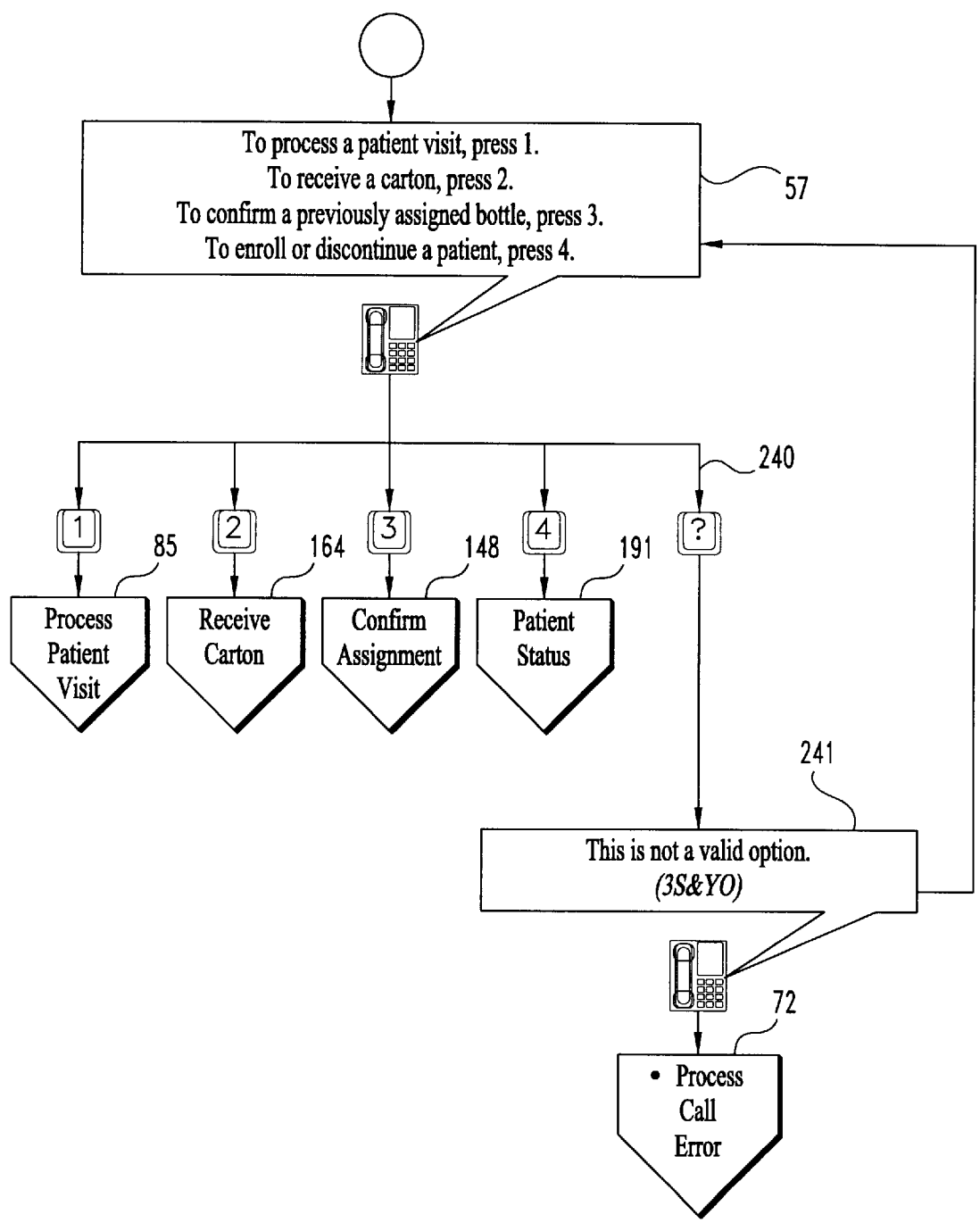

Referring back to FIG. 13, if the entered study ID and personal identification number are verified 70, the program returns to the Introduction (FIG. 4) and the Main Menu routine 84 is run. Referring to FIG. 18, the caller is given the option 57 to process a patient visit (by pressing 1), receiving a carton (by pressing 2), confirm a dosage assignment (by pressing 3), or administer patient status (by pressing 4). If the caller presses a button 240 other than buttons 1–4, she is given a predetermined number of attempts before being routed out of the program through the Process Call Error routine 72, as described above.

PROCESS PATIENT VISIT

Figure 15:
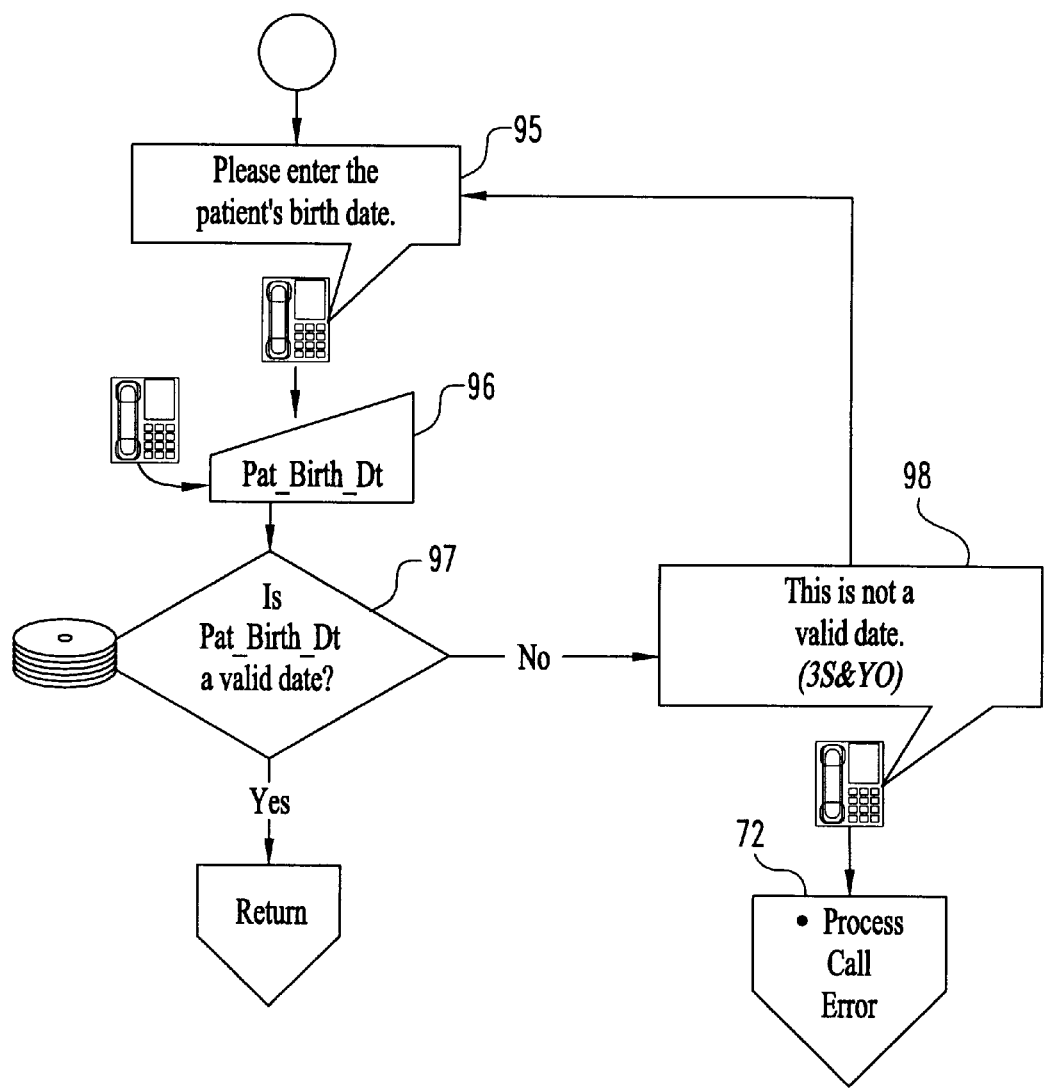
Figure 16:
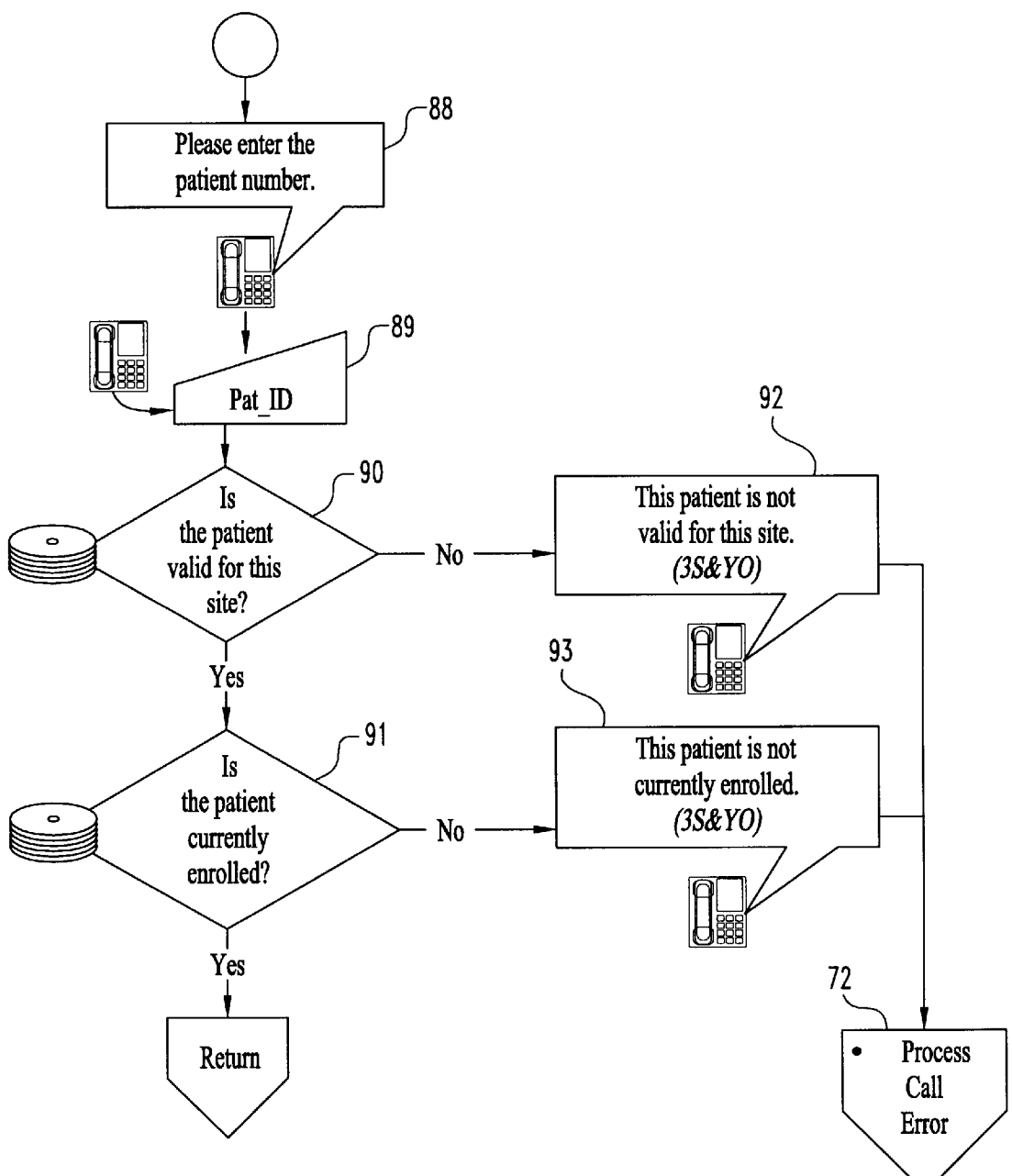
Figure 17:
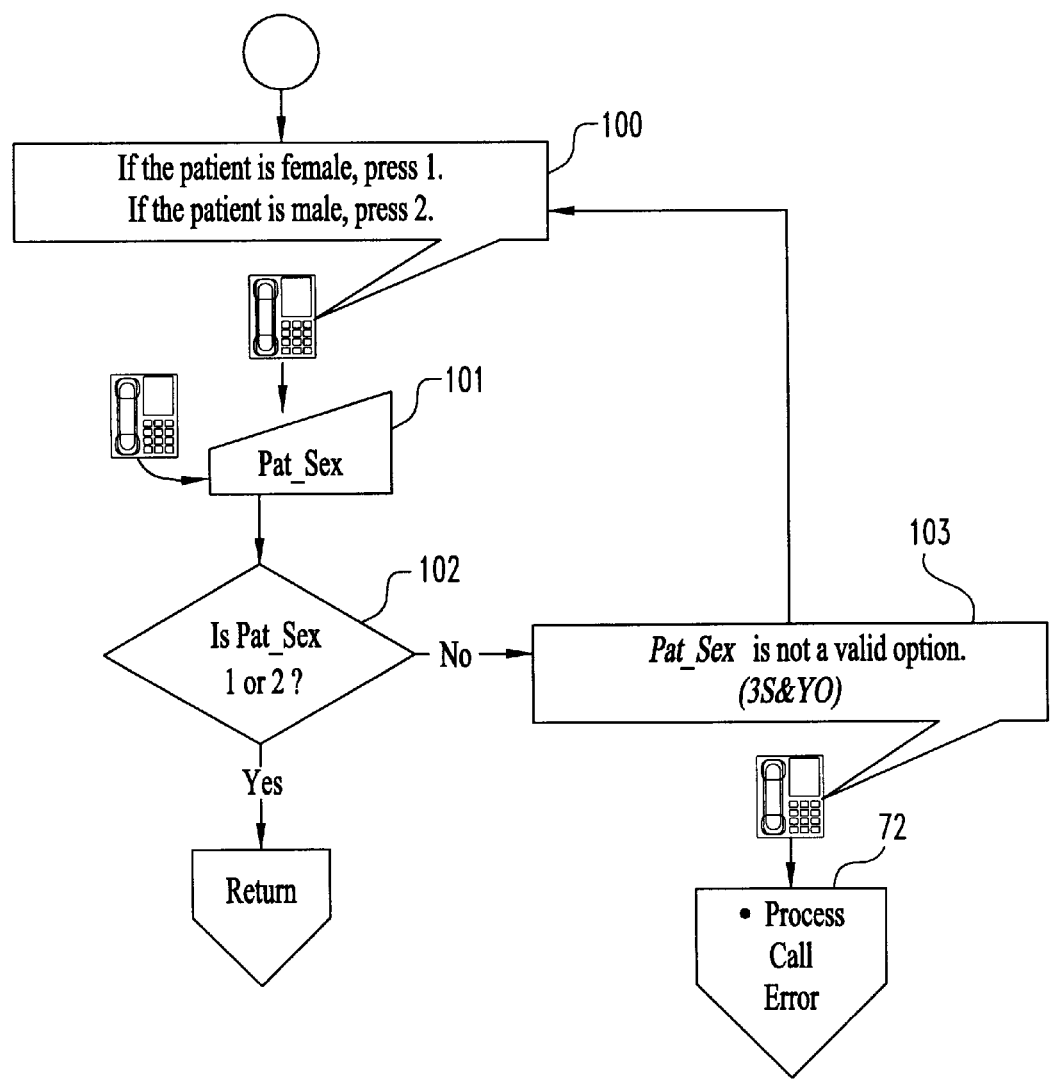
Figure 25:
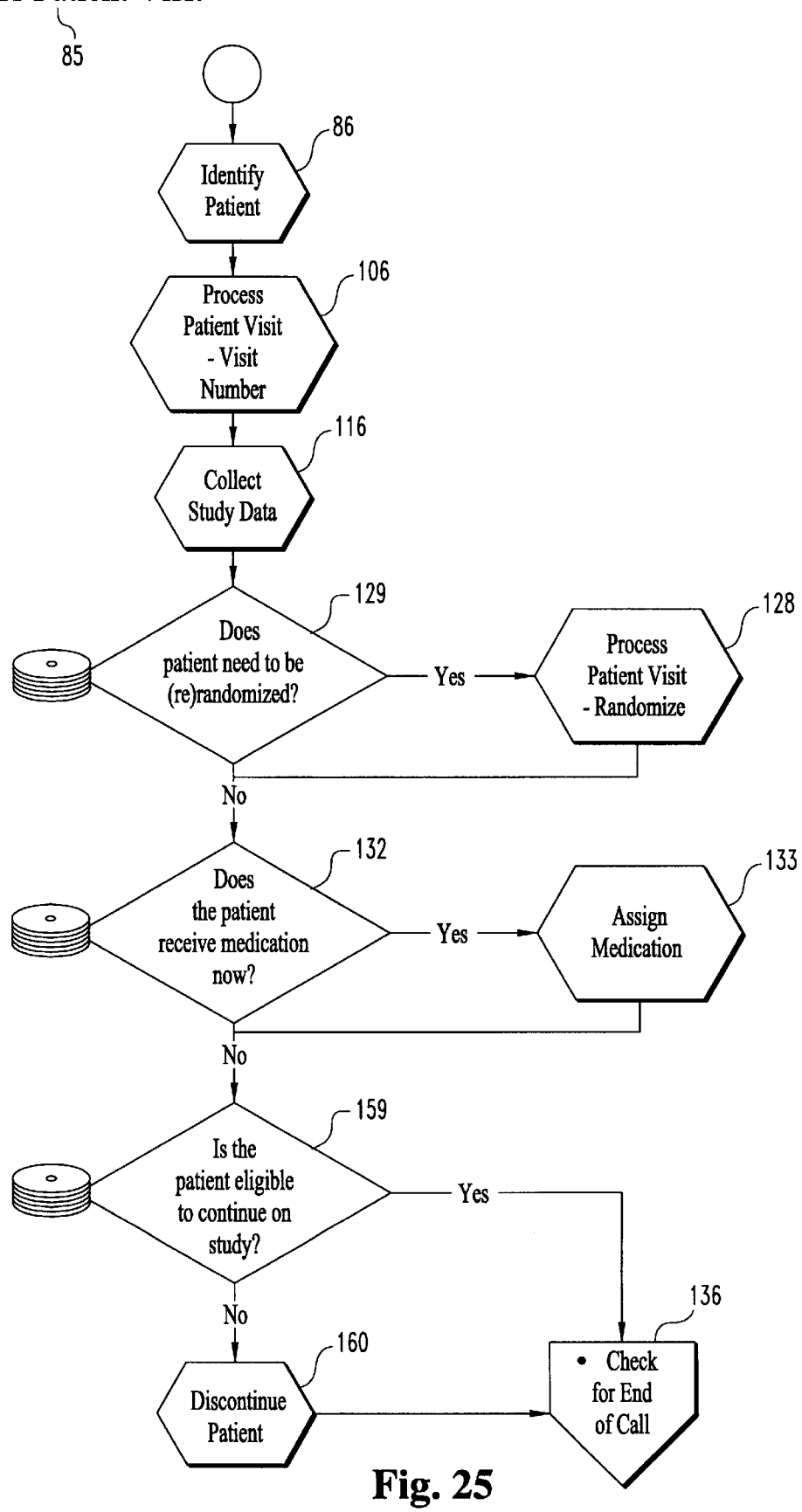

If the caller selects "Process Patient Visit" (FIG. 18), the Process Patient Visit routine 85 is run. Referring to FIG. 25, the Identify Patient routine 86 is first run (FIG. 14) which first runs, the Identify Patient—Patient ID routine 87. Referring to FIG. 16, the caller is first asked to enter the patient identification number 88. The caller enters the data at 89. If the patient is not valid for this site 90 or investigator or is not currently enrolled 91, the caller is so notified 92 and 93, respectively, and the program routes to the Process Call Error subroutine 72 (FIG. 31). If the patient is valid for this site or investigator and is currently enrolled, the program will go back to the Identify Patient subroutine 86 (FIG. 14), and the Identify Patient—Birth Date subroutine 94 is run. Referring to FIG. 15, the caller is asked to identify the patient's birth date 95. If upon entry of data by the caller 96, a valid date has not been entered 97, the caller is informed of this 98 and she is given a predetermined number of attempts before being routed out of the program through the Process Call Error Routine 72, as described above. If a valid date has been entered 97, the program returns to the Identify Patient subroutine 86 (FIG. 14), and the Identify Patient—Sex subroutine 99 is run. Referring to FIG. 17, the caller is requested to press either a 1 or a 2 to enter the six of the patient 100. Upon entry of the data by the caller 101, if an entry other than 1 or 2 is made 102, she is informed of the error 103 and she is given a predetermined number of attempts before being routed out of the program through the Process Call Error routine 72, as described above. If valid data has been entered, the program returns to Identify Patient 86 (FIG. 14), and it proceeds to match 104 the birth data and sex entered by the caller with the database records. If a match is not detected, the caller is apprised of this information 105 and she is given a predetermined number of attempts before being routed out of the program through the Process Call Error routine 72, as described above.

Figure 27:
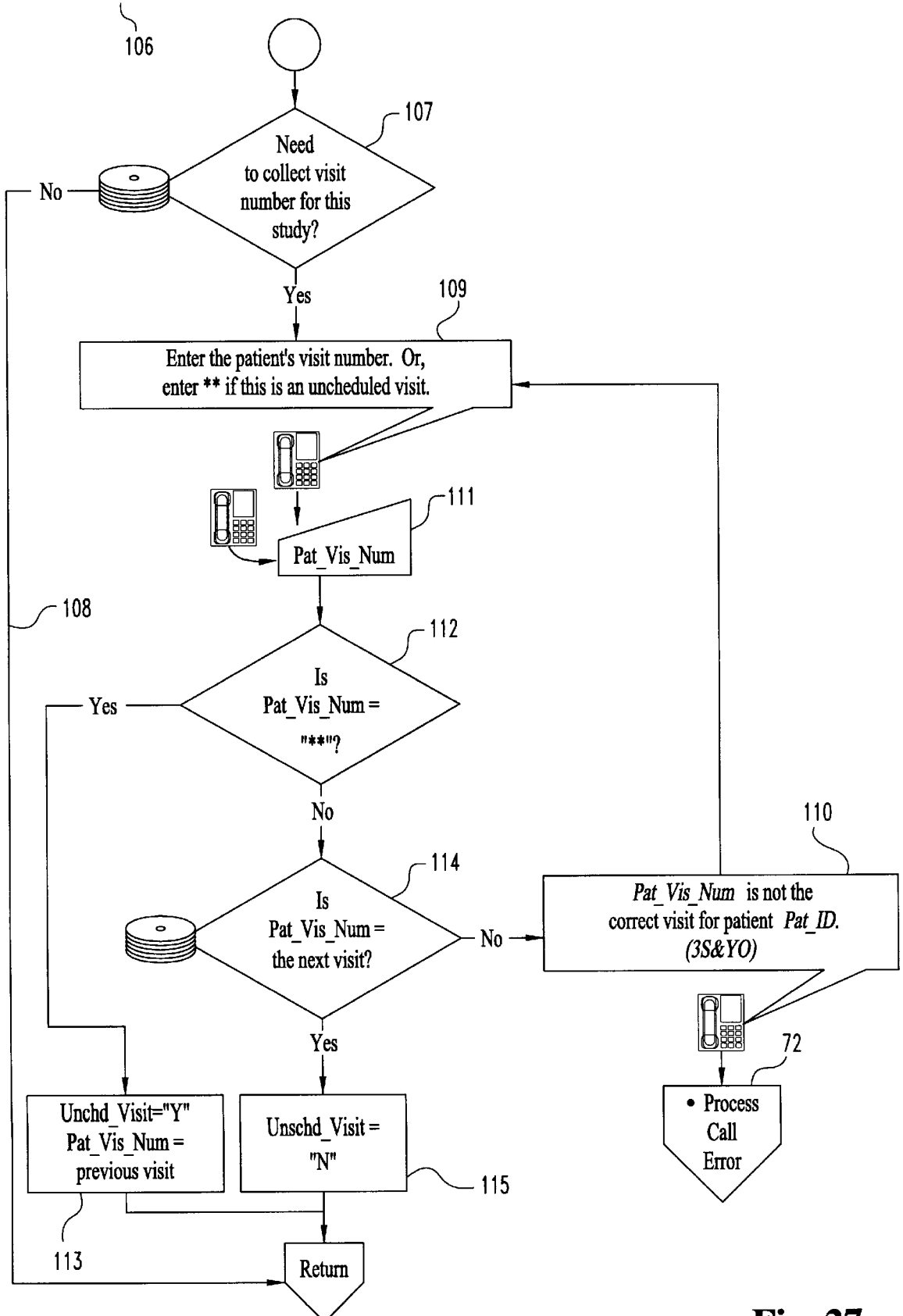

If the birth data and sex for this patient are matched, the program returns to the Process Patient Visit routine 85 (FIG. 25) and proceeds to the Process Patient Visit—Visit Number subroutine 106. Referring to FIG. 27, if the present study has been designed to run independently of the number of visits 107, this portion of the program is bypassed 108. If re-randomization, dose titration, general evaluation or other administrative or evaluative actions or reports are desired, the number of each patient visit is required and the caller is asked 109 to enter the patient visit number. Again, the caller is given a predetermined number of opportunities to enter the correct information, in this case, the next sequential visit number for that patient, (at 111) each time being apprised (at 110) of an error, before being routed to the Process Call Error subroutine 72, discussed above. The caller is also afforded an opportunity to enter information regarding a patient who is being examined during an unscheduled visit, in which case (at 112) a flat identified as "Unschd__Visit", is set to "Y" (at 113). If instead, the caller correctly identifies the visit number 114, the flag "Unschd Visit" is set to "N" (at 115). Data entered during unscheduled visits may or may not be incorporated into the overall study results, depending upon the manner in which the study was created and any standardized guidelines for conducting such studies.

Figure 7:
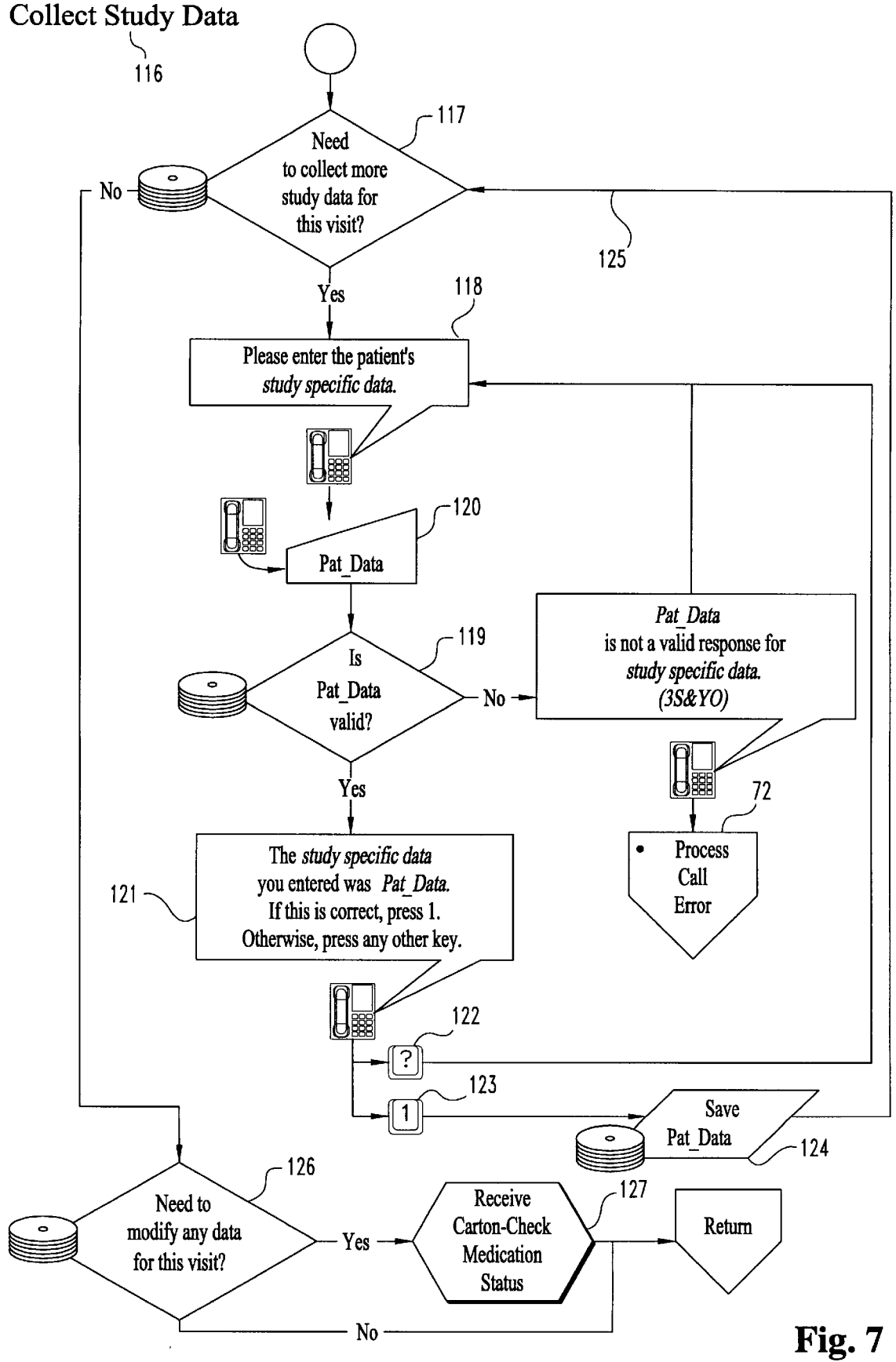

Upon completion of the Visit Number subroutine 106, the program returns to Process Patient Visit routine 85 (FIG. 25) and proceeds to the Collect Study Date subroutine 116. Referring to FIG. 7, as set up, the study may provide (at 117) for the collection of no data or a host of different data information. If information is required and has not yet been collected, the caller is asked to enter "study specific data" 118. In other words, for a particular study, the caller may be asked to enter the patient's score for the relevant test which has assessed the patient's progress in response to his treatment. Again, the caller is given a predetermined number of opportunities to enter the data in the correct format 119. The information entered by the caller (at 120) is repeated back and the caller is given the opportunity 121 to verify the entered information. If the information is not verified by the caller (at 122), she is permitted to reenter the data. Upon verification 123 and saving 124 the information, the sponsor computer advances (at 125) to any additional information which is requested. For example, the computer may now ask (at 118) for the patient's weight. Upon collection of all the data required by the study, the computer requests (at 126), if necessary, for modification to any of the data for this visit. Modification of visit data 127 (FIG. 8) is provided for at this step of the routine to account for studies in which certain criteria may change during the course of the study. Permitting modification by the caller investigator during the course of the study in response to either predetermined or unforeseen events permits completion of the study substantially as intended, and avoids having to either rerun the study or run another study to account for such changes or modifications.

Figure 26:
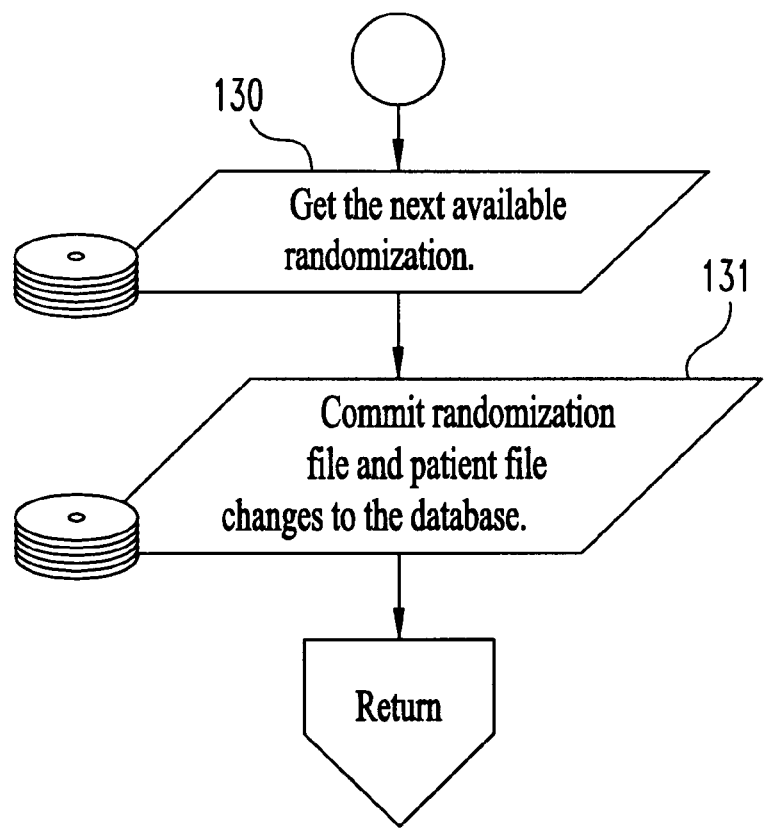

After completion of data collection from the caller through subroutine 116, the program returns to the Process Patient Visit routine 85 (FIG. 25) and re-randomization of the patient is conducted (at 128), if required (at 129) by the study parameters and if warranted by the collected data. Re-randomization of the patient may be called for in view of negative or no progress by the patient in response to his treatment. Referring to FIG. 26, and as described above, randomization is made possible during the course of the study because data can be collected and assimilated from all investigators and all study sites. If the predetermined criteria is met, the randomization routine 130 is modified in accordance with the study parameters and the progress of the study. The randomization routine 103 may be affected throughout the course of the entire study by the recorded progress of each patient. That is, upon completion of the study by one patient who is positively treated by the study drug at a particular dosage, the randomization routine 103 will be changed to increase the possibility for new patients to the study or for existing re-randomized patients to receive that medication.

Upon re-randomization of the subject patient, the new patient status and the modified randomization condition are committed to the database 131, and the program returns to the Process Patient Visit routine 85 (FIG. 25). Next, in the event that the patient is due to receive medication (i.e., if this is a scheduled visit), or if the patient is scheduled to receive medication at this visit as opposed to others (at 132), then medication is assigned through the Assign Medication subroutine 133.

Figure 5:
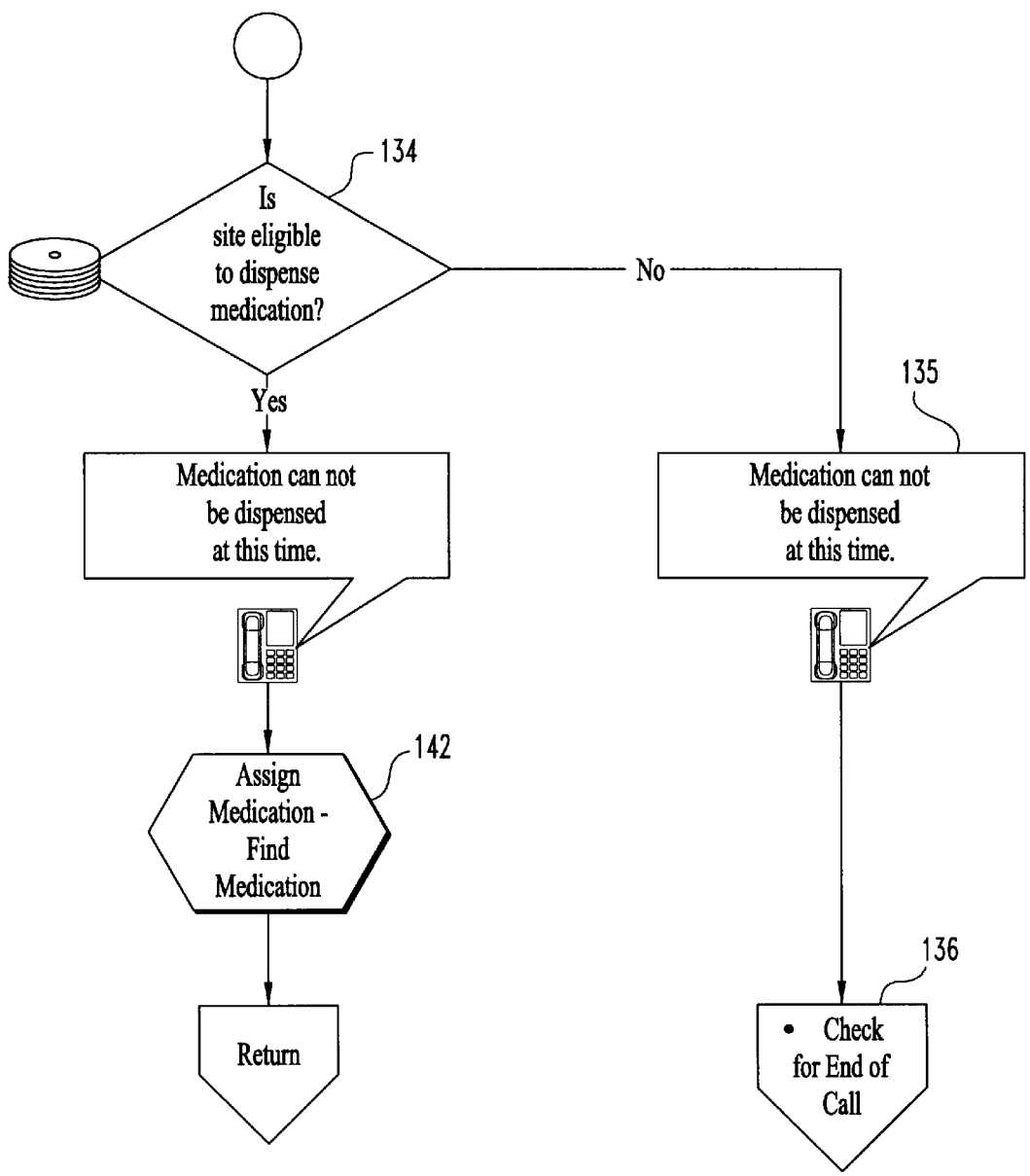
Figure 30:
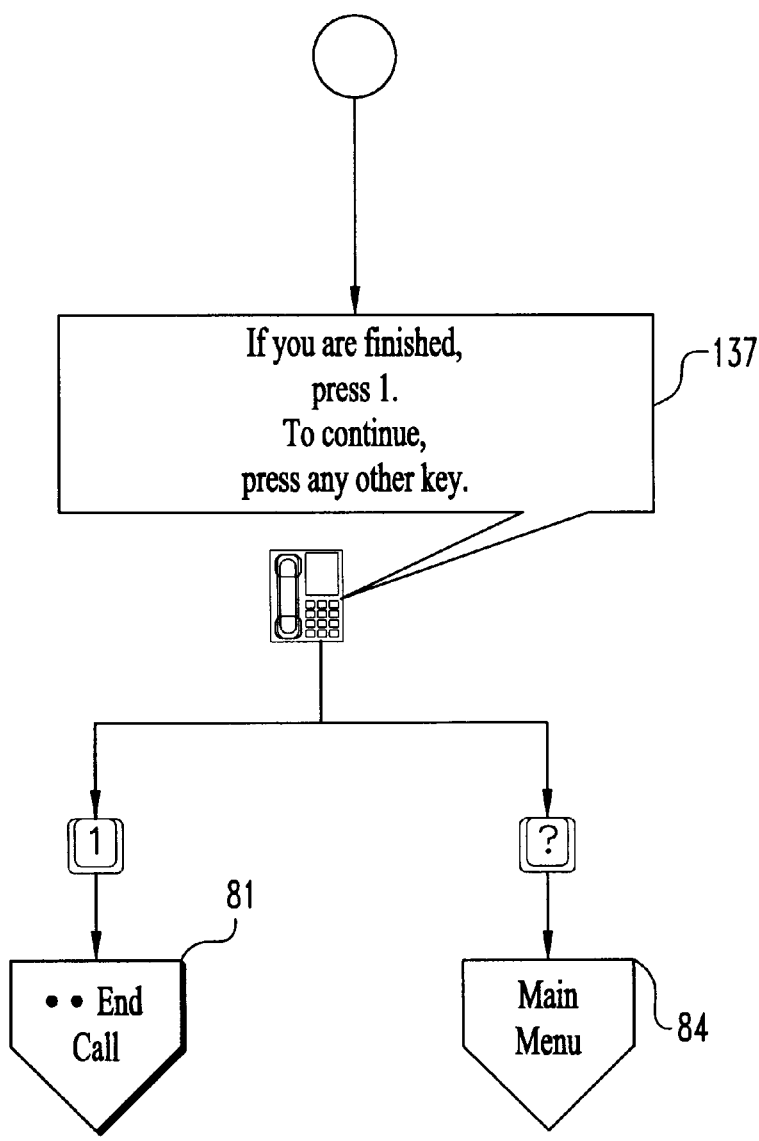

Referring to FIG. 5, in the event that this particular site is not eligible to dispense medication 134 (i.e., the caller may be authorized only to collect data but not to dispense medication), the caller is apprised of this 135 and the Check for End of Call subroutine 136 is run. Referring to FIG. 30, the caller is asked if she is finished with the call 137, whereupon either the End Call subroutine 81 is run, or the caller is returned to the Main Menu routine 84. Referring back to FIG. 5, if the site is eligible to dispense medication, the Assign Medication—Find Medication subroutine 142 is run.

Figure 6:
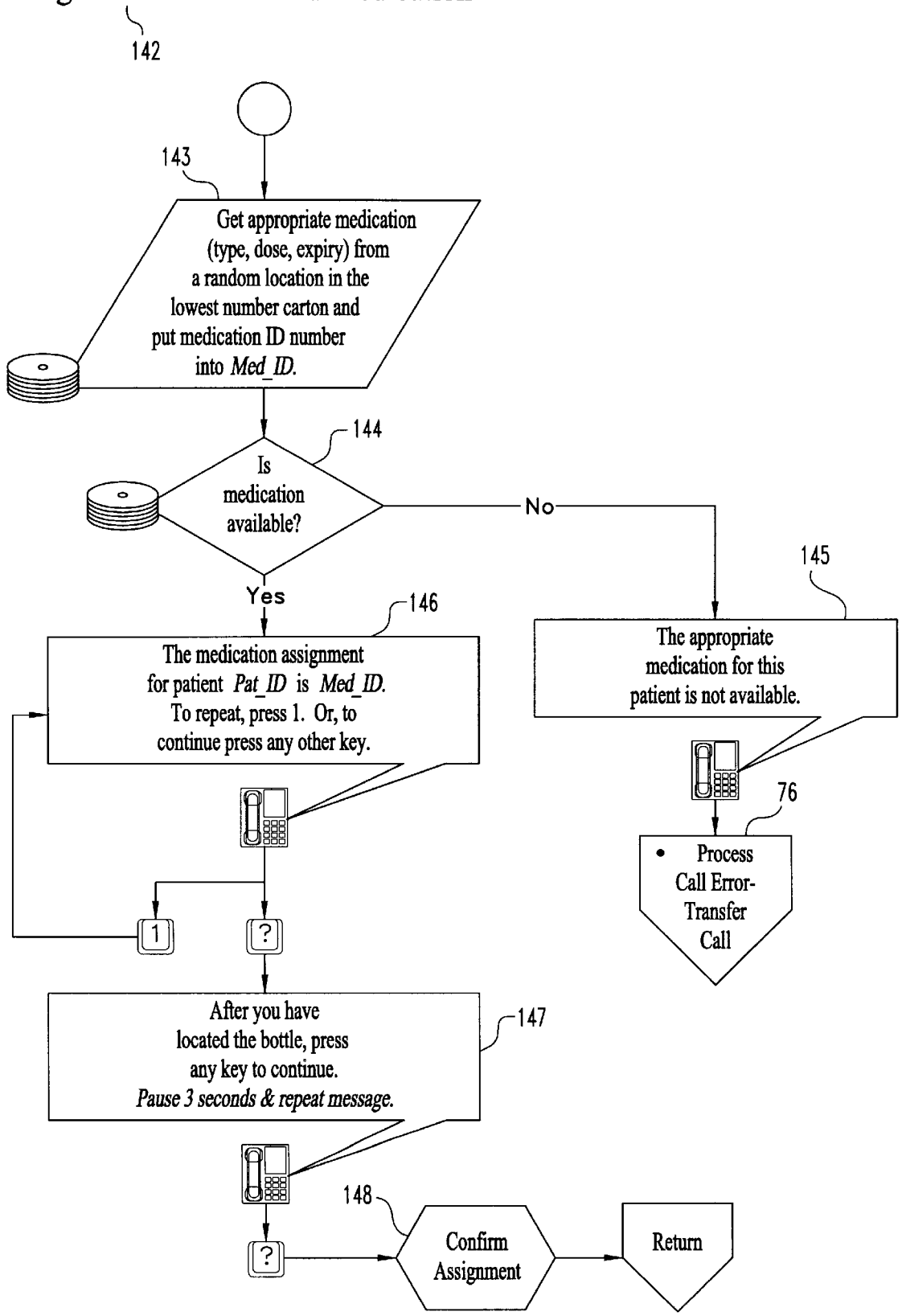

Referring to FIG. 6, the sponsor computer retrieves (at 143) the appropriate medication identification (type, dosage, expiry) from a random location in the lowest number carton of the caller investigator. The computer then checks (at 144) to make sure the medication is, in fact, available in the caller investigator's stock. That is, by monitoring the administration of medication from each investigator, the sponsor computer database will have a running record of all medication that the investigator has at any one time. In this fashion, the sponsor will both know whether or not a particular medication is available to be dispensed and whether replacement medication is needed to be sent to the investigator. In optimum circumstances, replacement medication should be delivered to the investigator well before the investigator runs out of a needed medication. In other circumstances, a particular desired medication may be discontinued from the study. In either case, the caller is apprised of this 145 and the Process Call Error—Transfer Call subroutine 76 is run. If the medication is available 144, the caller is apprised 146 of the ID number (BID number 58, FIG. 3) of the appropriate medication for that particular patient. The caller is permitted to have the information repeated as desired. After the caller has retrieved the assigned medication bottle, the caller presses any key to continue with the program 147 and to confirm assignment 148 of the bottle.

Figure 9:
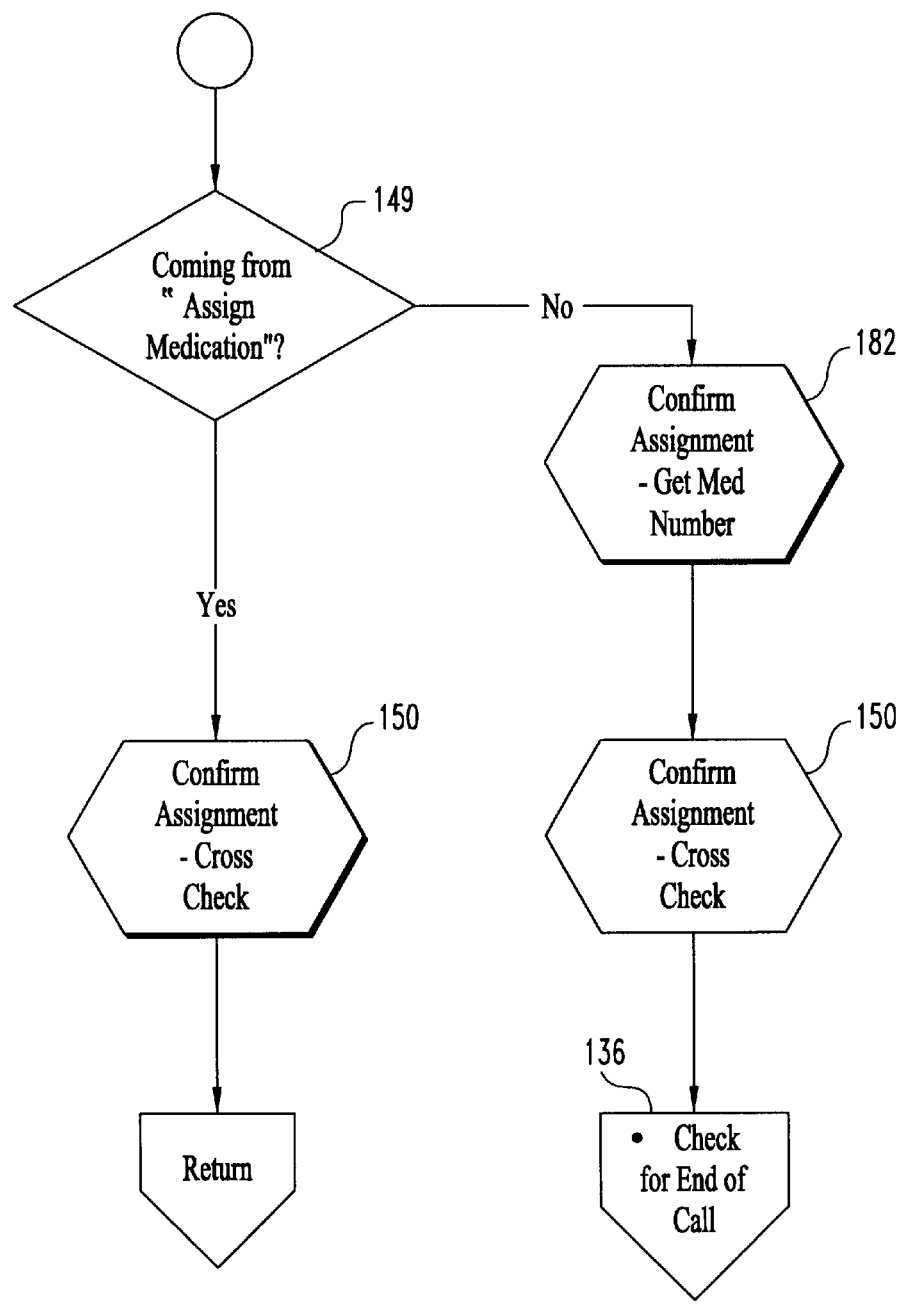
Figure 10:
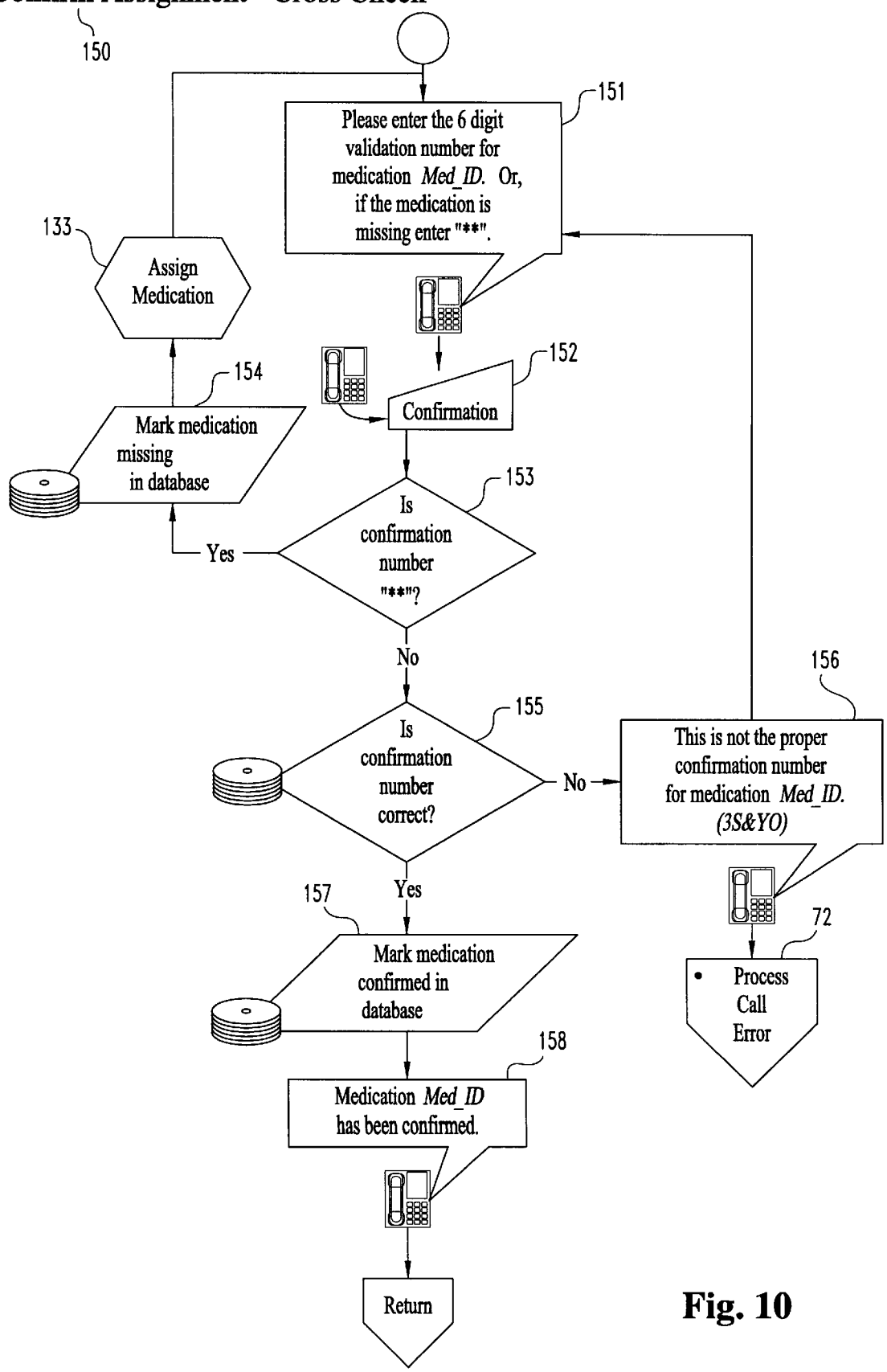

Referring to FIG. 9, having just initially assigned the medication, the sponsor computer proceeds (at 149) to the Confirm Assignment—Cross Check subroutine 150. Referring to FIG. 10, the caller is asked 151 to enter a six digit validation number (CPID number 59, FIG. 3) or to identify if the specified medication is missing. If the caller identified (at 152) that the medication was missing 153, this fact is noted to the computer database 154 and the Assign Medication subroutine 133 is restarted as described above and in FIG. 5. If instead the caller enters an incorrect validation number 155, she is apprised of this fact 156 and is given a predetermined number of attempts before being routed out of the program through the Process Call Error routine 72, as described above. If the correct validation number was input by the caller 155, the computer notes in its own database that the correct medication has been identified 157 and further apprises the caller of this fact 158. The assignment of the medication is now complete and the program returns to subroutine 148 (FIG. 9), to subroutine 142 (FIG. 6), to subroutine 133 (FIG. 5), and finally to subroutine 85 (FIG. 25).

Referring back to FIG. 25, the patient has been properly identified 86, his visit has been processed 106, specific data has been collected 116, (re-)randomization has been performed (if necessary) 129, and medication has been assigned (if proper) 133. Now the decision is made as to whether the patient should continue the study 159. This decision may be based upon pre-assigned parameters such as the specific improvement or worsening of a patient's condition, or it may be based upon ongoing monitoring and analysis of the sponsor for a variety of other reasons. If the patient is no longer eligible to continue in the study 159, the patient is discontinued 160.

Figure 12:
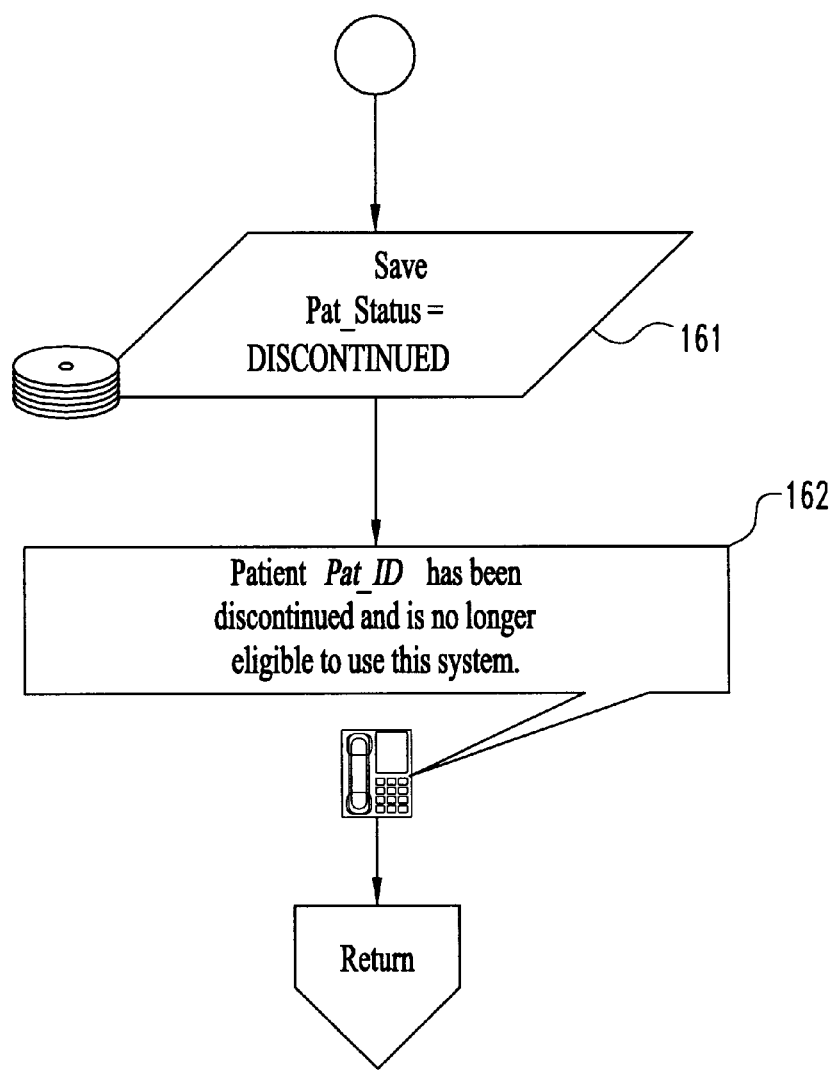

Referring to FIG. 12, the status of the patient as discontinued is saved 161 in the computer database and the caller is apprised that the patient is being discontinued and is no longer eligible to participate in the study 162. Referring back to FIG. 25, the patient is determined to continue in the study 159, the Check for End of Call subroutine 136 (FIG. 30) is run, as described above.

RECEIVE CARTON

Figure 28:
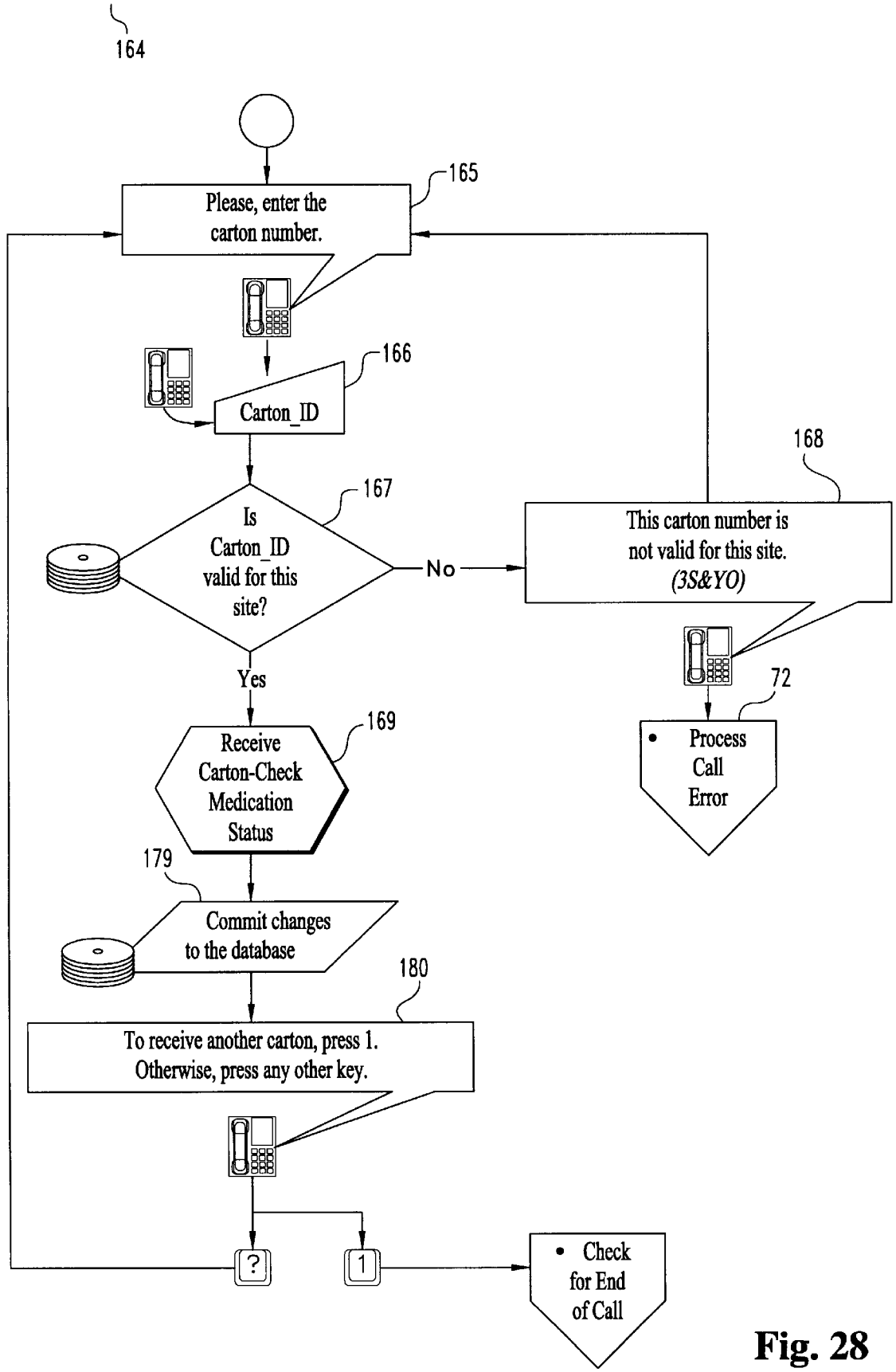

Referring back to FIG. 18, the caller's second option 164 is to receive a carton, this procedure being exercised upon initial receipt of the study material as well as upon receipt of replacement materials. Referring to FIG. 28, the caller is first asked (at 165) to enter the carton number appearing on the exterior of the carton. Upon entry of that number 166, the sponsor computer verifies 167 that this carton identification number is the correct number for the caller's site. If it is not, the caller is apprised of the error 168 and she is given a predetermined number of attempts before being routed out of the program through the Process Call Error routine 72, as described above. If the correct number is input by the caller, the Receive Carton—Check Medication Status subroutine 169 is run to verify the carton's status.

Figure 29:
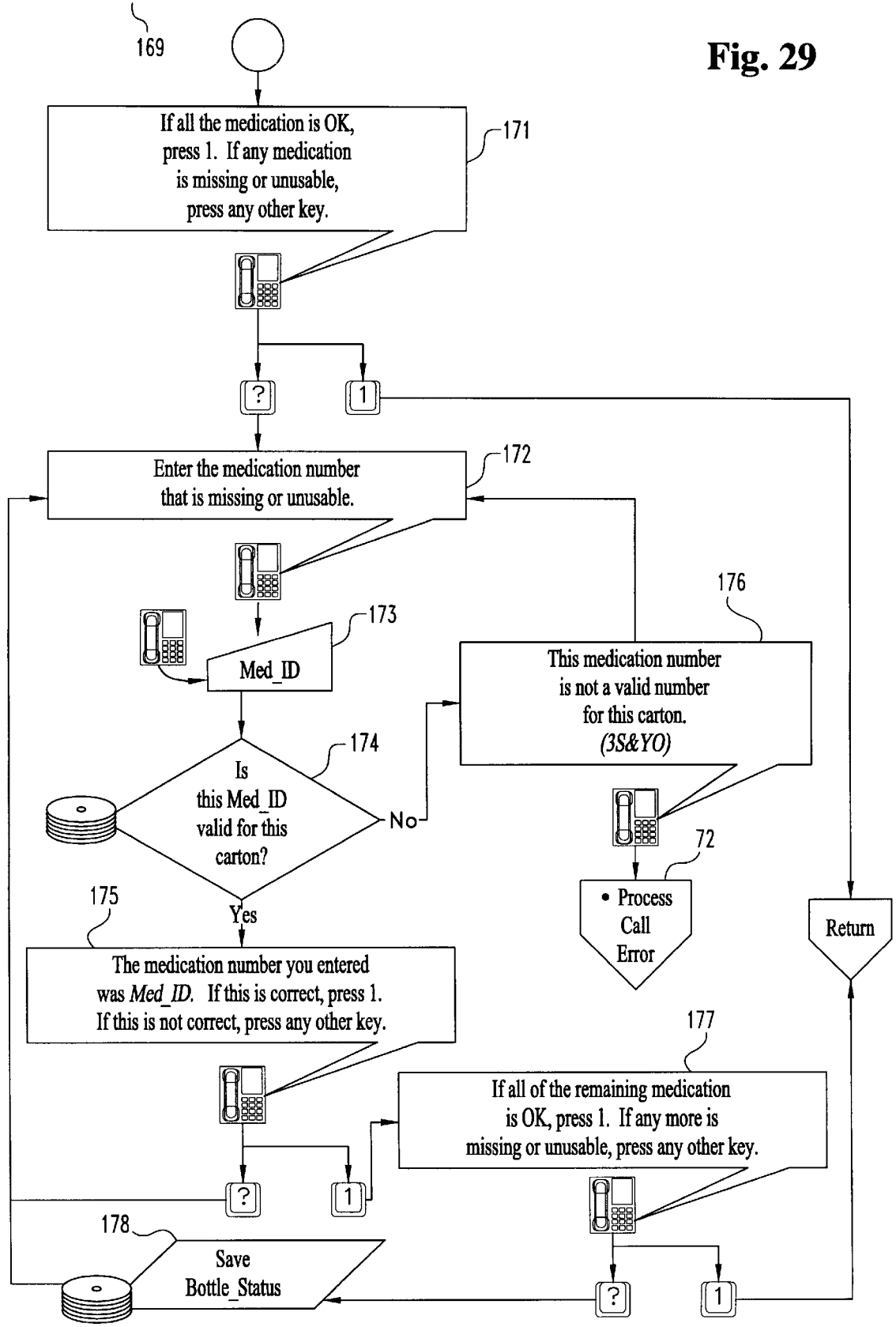

Referring to FIG. 29, the caller is asked (at 171) to check the carton and verify that all the medication is present and in good condition. If it is not, the caller is asked (at 172) to identify which medication is missing or unusable. Upon entry (at 173) through the telephone keypad of the bad or missing medication ID numbers by the caller, the computer verifies at 174 that the inputted information is valid for that carton, and it then confirms 175 the number of the missing or unusable medication. Again, if the caller enters invalid numbers, she is apprised of this 176, and she is given a predetermined number of attempts before being routed out of the program through the Process Call Error routine 72, as described above. Once the caller has verified 177 that all other bottles are OK and each bottle status has been saved 178, the sponsor computer returns to the Receive Carton routine 164 (FIG. 28), and all changes are saved to the database 179. The caller is then permitted to "receive" another carton 180. After the caller has completed receiving each carton, she is returned back to the Main Menu (FIG. 18).

CONFIRM ASSIGNMENT

Figure 11:
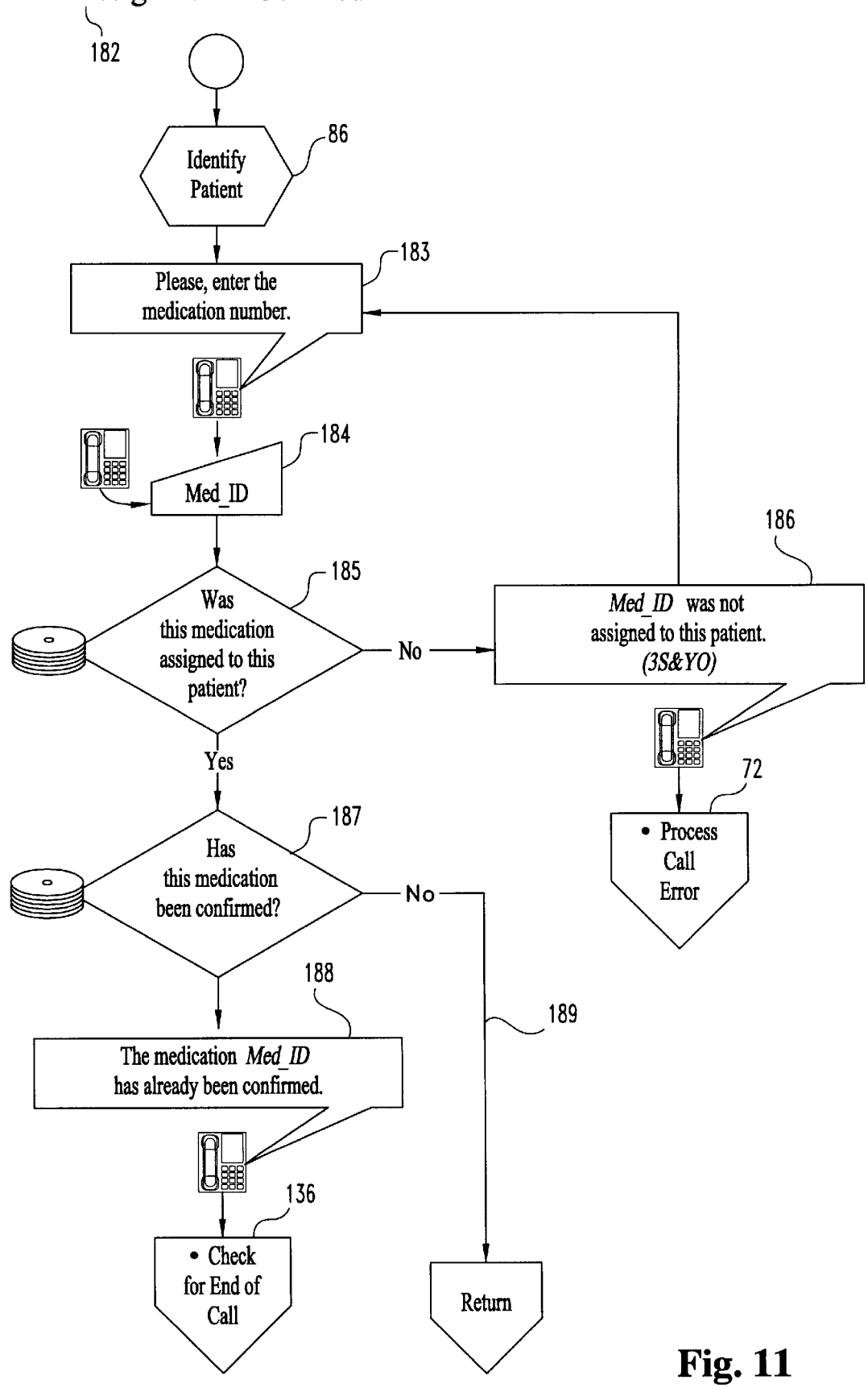

A third option for the caller in the Main Menu 84 is to confirm assignment 148 of a previously assigned medication. Referring again to FIG. 9, the sponsor computer, recognizing at 149 that this "confirm assignment" subroutine was not accessed from the "Assign Medication" subroutine, proceeds to the Confirm Assignment—Get Med Number subroutine 182. Referring to FIG. 11, the patient must first be identified through the Identify Patient subroutine 86 (FIG. 140, previously describe. The caller is then asked (at 183) to enter the medication number. After the caller inputs 184 the medication number that she desires to have confirmed, the sponsor computer determines 185 whether this medication was previously assigned to this patient. If it was not previously assigned, the caller is apprised of this 186 and she is given a predetermined number of attempts before being routed out of the program through the Process Call Error routine 72, as described above. If the sponsor computer determines 187 that this medication has already been confirmed, the caller is apprised of this fact 188 and the Check for End of Call routine 136 is run, giving the caller an opportunity to select another menu option as described above and shown in FIG. 30. If the medication has not previously been confirmed 189, the program returns to the Confirm Assignment routine 148 (FIG. 9) and then runs the Confirm Assignment—Cross Check subroutine 150 (FIG. 9, as described above and shown in FIG. 10). Once confirmation is thus completed, the caller is given the opportunity to select another option from the menu or end the call through the Check for End of Call subroutine 136 (FIG. 30).

PATIENT STATUS

Figure 19:
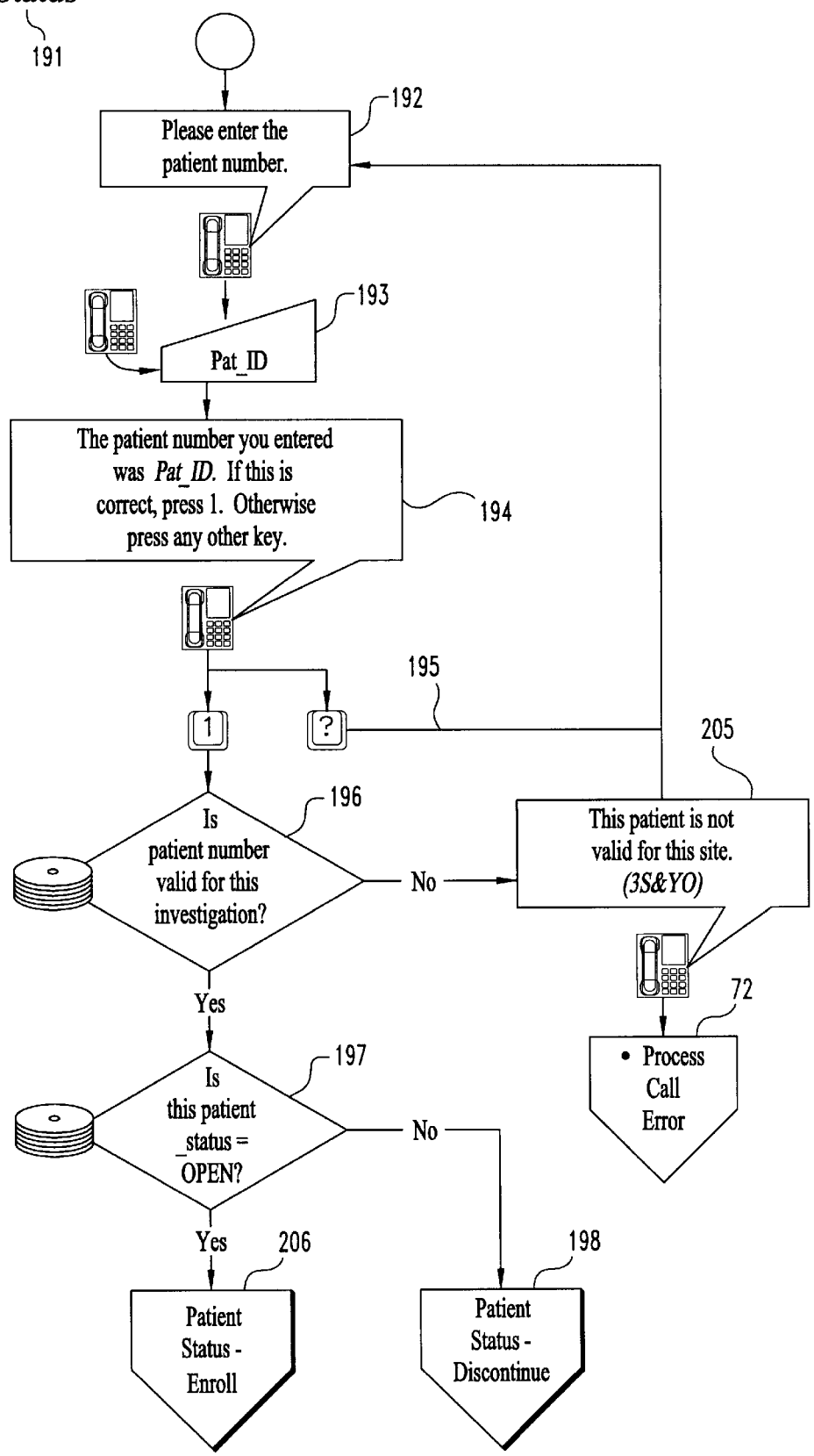

Referring back to FIG. 18, the fourth option for the caller is to administer the Patient Status 191. Referring to FIG. 19, the caller is asked (at 192) to enter the patient number. Upon entry 193 of that number, the sponsor computer repeats the number back to the caller 194, and the caller is asked to verify that number. If the number is incorrect, the caller presses any key other than "1" and is permitted to try again 195, or, if the caller presses "1", but the patient number is determined by the sponsor computer not to be valid for this investigation 196 (that is, has this patient previously been screened and approved for participation in the study), the caller is apprised of this 205 and she is given a predetermined number of attempts before being routed out of the program through the Process Call Error routine 72, as described above. If the patient number is valid for this investigation, the sponsor computer determines whether the "patient_status" is "OPEN" 197. The patient status is open if the study can currently accommodate additional patients. The study will have been designed to include a set number of patients, and once those patients are enrolled, no additional patients will be admitted. If the study design permits, patients may complete the study, thereby leaving vacancies for new patients to be enrolled. If it is determined that the patient status is not open, the open option available to the caller is the Patient Status—Discontinue subroutine 198.

Figure 20:
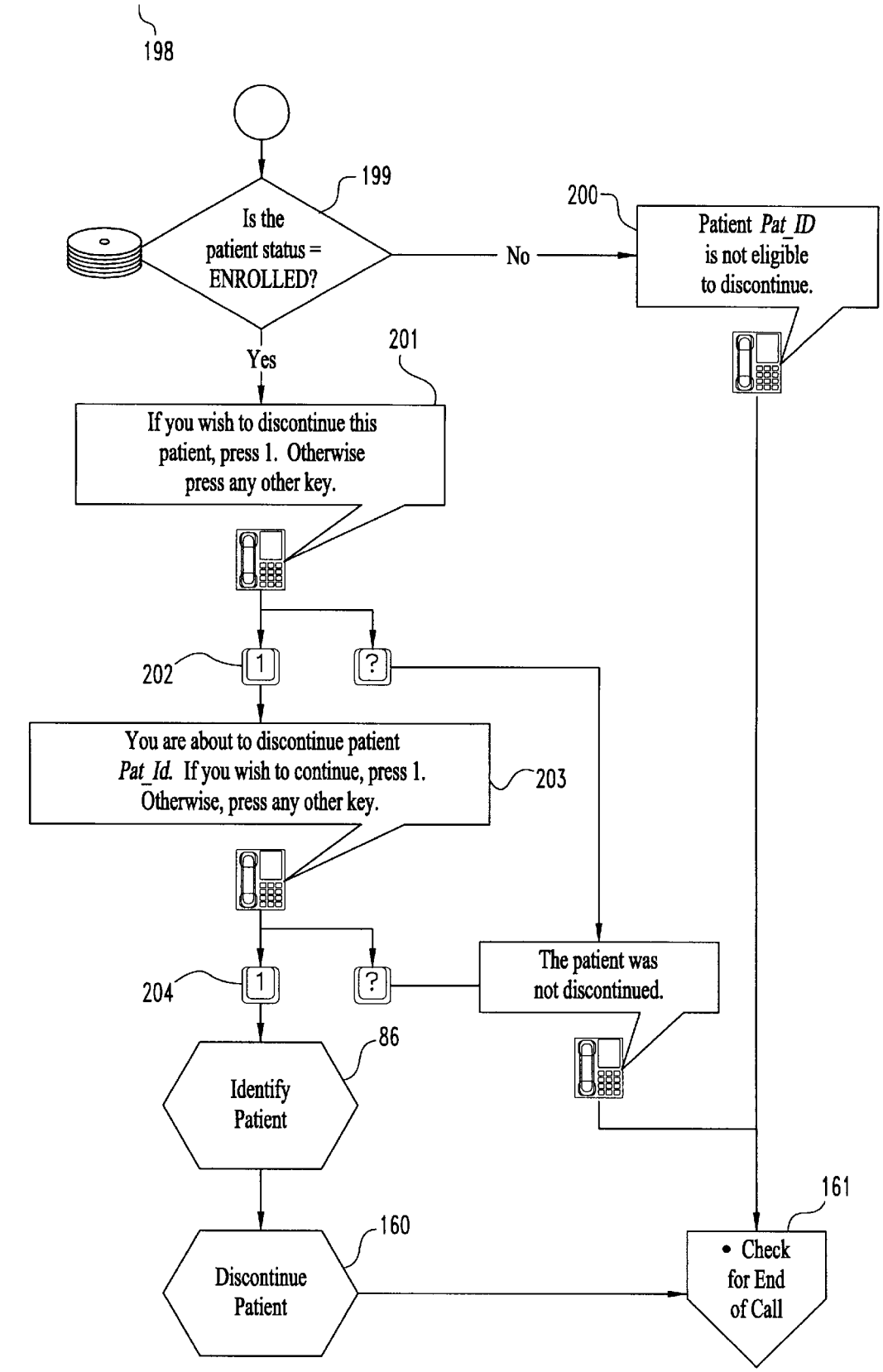

Referring to FIG. 20, if the patient at issue is not currently enrolled 199, the caller is apprised of this fact 200, and the Check for End of Call subroutine 136 (FIG. 30) is run. If the patient is enrolled 199, the caller is given the option (at 201) to discontinue the patient. After the caller has entered her selection 202, she is asked to verify discontinuation of the patient 203. Upon confirmation (at 204) that the caller wishes to discontinue the specified patient ID, the caller is required to fully identify the patient by the running of the Identify Patient subroutine 86 as described above and shown in FIG. 14. Thereafter the Discontinued Patient subroutine 160 is run as described above and shown in FIG. 12, followed by the Check for End of Call subroutine 136.

Figure 21:
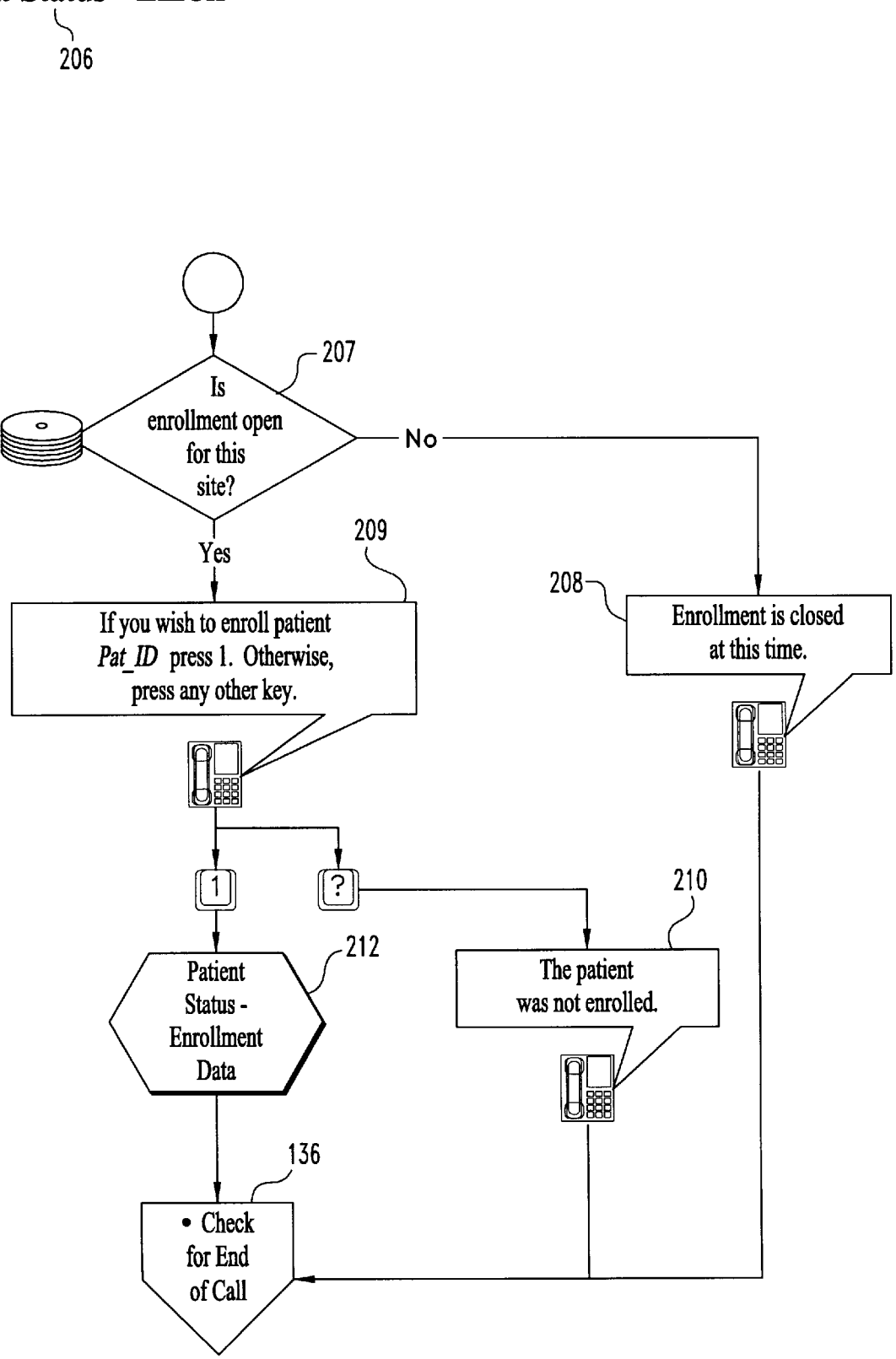

Referring back to FIG. 19, if the patient status is open 197, the caller is permitted to enroll a patient through the Patient Status Enroll subroutine 206. Referring to FIG. 21, if the current site is not open for enrollment 207, the caller is apprised of that fact 208 and the Check for End of Call subroutine 136 (FIG. 30) is run. If the site is open for enrollment 207, the caller is asked if she wishes to enroll a patient 209. If she does not wish to enroll a patient 210, the Check for End of Call subroutine 136 is run. If the caller does verify she wishes to enroll a patient, the Patient Status—Enrollment Data subroutine 212 is run.

Figure 22:
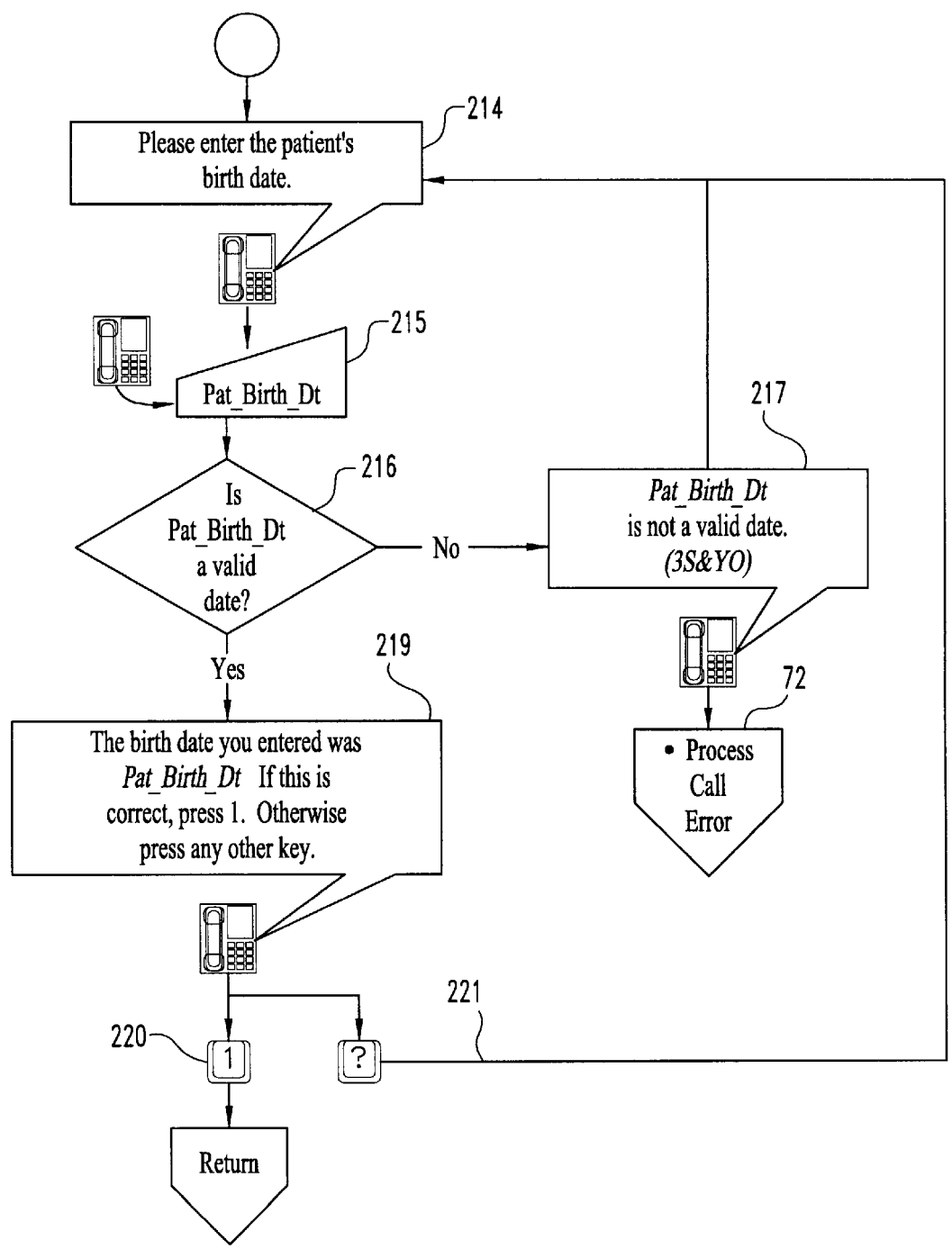
Figure 23:
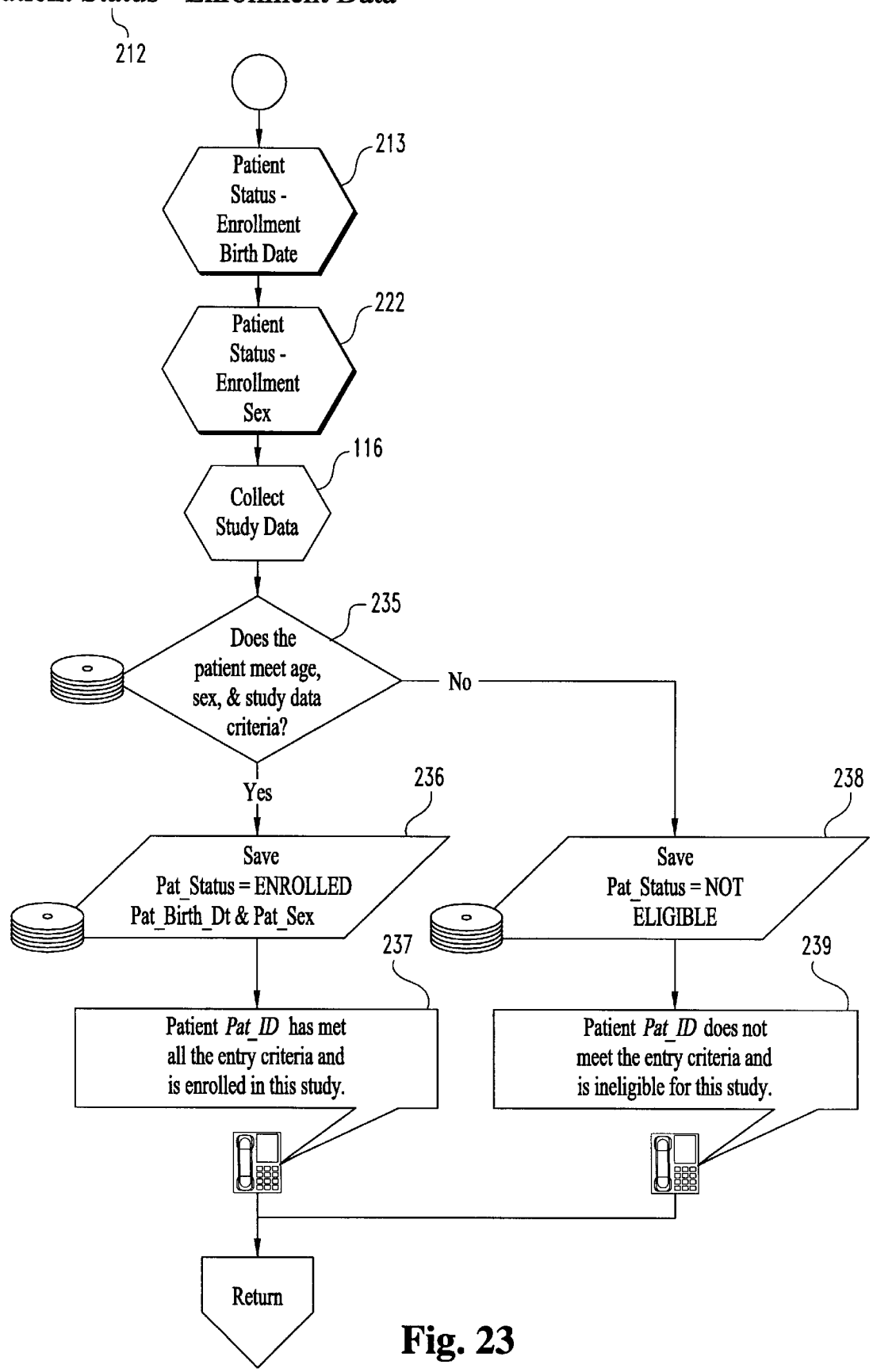

Referring to FIG. 23, the patient's birth date is first obtained through the Patient Status—Enrollment Birth Date subroutine 213. Referring to FIG. 22, the caller is asked to identify the patient's birth date 214. Upon entry 215 of the birth date, the sponsor computer verifies that a valid date has been entered 216, and if not, the caller is apprised of this fact 217, and she is given a predetermined number of attempts before being routed out of the program through the Process Call Error routine 72, as described above. If a valid date has been entered 216, the computer repeats the entered birth date and requests verification 219, which is verified by the caller by pressing a predetermined key on the telephone, as shown at 220. Pressing any other key returns the caller at 221 to the top of the Patient Status-Enrollment Birth Date subroutine 213. Upon verification 220, the program returns the caller to the Patient Status—Enrollment Data subroutine 212 (FIG. 23).

Figure 24:
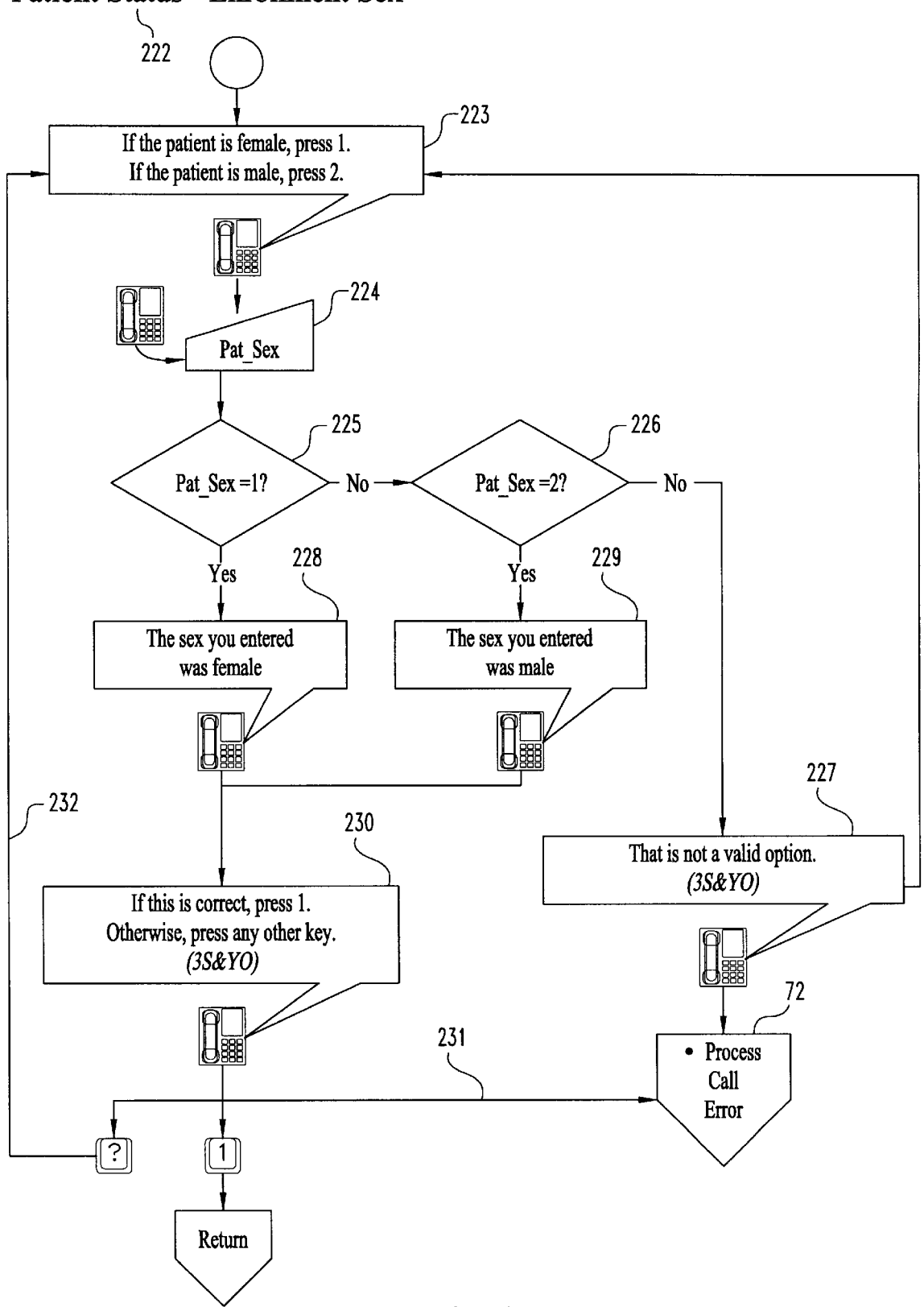

Referring back to FIG. 23, after proper entry of the patient's birth date, the patient's sex is entered through the Patient Status—Enrollment Sex subroutine 222. Referring to FIG. 24, the caller is asked to identify whether the patient is a female or a male 223. Upon entry 224 of the data by the caller pressing the designated keys on the telephone keypad, the sponsor computer verifies that the entered response is one of the offered choices (225, 226). If it was not, the caller is apprised of this 227 and she is given a predetermined number of attempts before being routed out of the program through the Process Call Error Routine 72, as described above. The sponsor computer then verifies input by repeating the selection (228, 229) and asking the caller (at 230) to verify the selection. If the selection is not verified, the caller is given a predetermined number of opportunities to enter the correct information (231, 232) as discussed above, before the Process Call Error subroutine 72 is run. If the selection is correct, the caller is returned to the Patient Status—Enrollment Data subroutine 212 of FIG. 23, where the Collect Study Data subroutine 116 is run as described above and shown in FIG. 7, to allow for study specific data to be entered 118, or modification to any data to be made 126. Thereafter, the program returns to the Patient Status—Enrollment Data routine 212 of FIG. 23. If the patient meets the age, sex, and study criteria 235 as determined by the authors of the study, the sponsor computer saves the relevant enrollment data 236, the caller is apprised that the patient has been enrolled in the study 237, and the program is returned to the Patient Status-Enroll subroutine 206 (FIG. 210 and directed to the Check for End of Call subroutine 136. If the age, sex, and study criteria 235 are not met, the sponsor computer saves the relevant "not eligible" status of this patient 238 and the caller is apprised that the patient is not eligible for this study 239. The caller is then again returned to the Patient Status—Enroll subroutine 206 (FIG. 21), and then to the Check for End of Call subroutine 136.

Referring back to FIG. 18, if the caller enters an invalid option 240, the caller is apprised of this fact 241 and she is given a predetermined number of attempts before being routed out of the program through the Process Call Error routine 72, as described above.

The present invention offers a broader platform upon which clinical trials may be run. Data may be collected, assimilated and applied, during the study to adaptively randomize the new patients entering the study and to change individual treatments, again during the study, either by dose titration or re-randomization, for those patients who have not shown sufficient improvement. Importantly, such adaptive randomization, re-randomization and dose titration can be accomplished in a common triple blinded study, that is, with hundreds of patients, multiple medications and/or multiple dosages, but without any of the physician investigators, patients or sponsors knowing when or what medication or randomization changes are occurring. The present invention further precludes the inadvertent selection of the incorrect medication package or bottle by providing for two separate identifying numbers of the bottles. Integrity of the study can thereby be maintained. Previously, the investigator could be told the bottle number and she would write it down. The sponsor's records would indicate that the medication was administered, but the investigator could then have selected the wrong bottle because she lost or misread the paper she wrote the number on, or because she wrote down the wrong number. Since all the bottles in a study may not be used, the incorrectly administered bottle might never be missed, and the study integrity is comprised without anyone ever knowing. Here, the investigator must enter the correct, corresponding confirmation number 59 to continue with the study. Failure to do so will result in an immediate error message to be issued to the sponsor. Likewise, the enrollment criteria of each patient participant must be received from the investigator and must match up with previously identified information to permit patient enrollment. Also, because the present invention permits for the entry of an unlimited range of study specific data 118 (FIG. 7), the instantaneous progress of the study can be had at any moment which, as discussed, allows for modification of study parameters on the fly, and, perhaps more importantly, for early warning of serious complication associated with the study drug. All these elements, alone or in combination, comprise a more efficient, more reliable, faster, safer and more diverse vehicle for conducting clinical trial studies.

While the invention has been illustrated and described in detail in the drawings and foregoing description, the same is to be considered as illustrative and not restrictive in character, it being understood that only the preferred embodiment has been shown and described and the all changes and modifications that come within the spirit of the invention are desired to be protected.

What is claimed is:

1. A method for administering clinical trial material in a study, comprising the step of:

providing at least one carton containing a plurality of bottles, each bottle having two separate identifying indicia appearing thereon, at least one of said bottles containing a quantity of clinical material at a first dosage, and another at least one of said bottles containing one of a quantity of said clinical material at a second dosage, a quantity of control drug and a placebo and wherein each of said indicia of each of said plurality of bottles is unique within the study;

identifying at last first and second study groups, each having a treatment schedule for administering dosages of at least one of said clinical material, said control drug and said placebo;

randomly assigning patients to said first and second study groups;

assigning at least one investigator to administer the contents of said plurality of bottles to said patients, said investigator having access to telephone means, said telephone means having a keypad and being for inputting and receiving information;

providing sponsor computer means including telephone capabilities and for storing information, for disseminating information and instructions over the telephone to said investigator, and for receiving information and instructions over the telephone from said investigator, said computer means operable, upon being contacted by said investigator, to identify which of said plurality of bottles of said at least one carton is to be administered to an identified one of said patients by reciting one of said two separate identifying indicia appearing on the selected bottle, but requiring said investigator to confirm selection of the correct bottle by requesting the investigator to enter into the telephone keypad the other of said two identifying indicia appearing on the selected bottle; and distributing said at least one carton to said investigator.

2. The method for administering clinical trial material of claim 1, wherein said first and second study groups have different treatment schedules.

3. The method for administering clinical trial material of claim 1, wherein said providing sponsor computer means step includes said computer being operable to collect information from said investigator over the telephone about a specific patient and to immediately thereafter instruct said investigator which bottle to administer, said instruction of which bottle to administer being based upon the collected information and predetermined study criteria.

4. The method for administering clinical trial material of claim 3, wherein said providing sensor computer means step includes said computer being operable during the course of a study to titrate the dosage of the clinical material it instructs the investigator to administer, said titration being based upon the information received from said investigator and upon predetermined study criteria.

5. The method for administering clinical trial material of claim 3, wherein said providing sponsor computer means step includes said computer being operable during the course of a study to re-randomize the specific patient to one of said at least first and second study groups, said re-randomization being based upon the information received from said investigator and upon predetermined study criteria.

6. The method for administering clinical trial material of claim 3, wherein said providing sponsor computer means step includes said computer being operable during the course of a study to adaptively randomize entry of new patients to one of said study groups in said randomly assigned step, said adaptive randomization being based upon the information received from said investigator and upon predetermined study criteria.

7. The method for administering clinical trial material of claim 6, wherein said providing sponsor computer means step includes said computer being operable to titrate the dosage of the clinical material it instructs the investigator to administer and re-randomize the specific patient to one of said first and second study groups, said titration and re-randomization being based on the information received from said investigator and upon predetermined study criteria, said computer being operable to perform dose titration, re-randomization of patients and adaptive randomization of new patients during an on-going study.

8. The method for administering clinical trial material of claim 6, wherein said providing sponsor computer means step includes said computer being operable during the course of a study to enroll a patient, said patient enrollment being accepted or rejected based upon the information received from said investigator and upon predetermined study criteria.

9. The method for administering clinical trial material of claim 6, wherein said providing sponsor computer means step includes said computer being operable during the course of a study to collect information from and issue instructions to the investigator identifying bad or missing bottles and being operable during the course of a study to direct issuance of replacement bottles therefor.

10. The method for administering clinical trial material of claim 6, wherein said providing sponsor computer means step includes said computer being operable during the course of a study to direct issuance of replacement bottles to an investigator before said investigator runs out of bottles of one of the first dosage, the second dosage, the control drug and the placebo.

11. The method for administering clinical trial material of claim 1 wherein the administering of clinical material is one of double blinding and triple blinding.

* * * * *